(12) United States Patent
Muchhala et al.

(10) Patent No.: US 12,097,032 B2
(45) Date of Patent: *Sep. 24, 2024

(54) MACHINE DIFFERENTIATION OF ABNORMALITIES IN BIOELECTROMAGNETIC FIELDS

(71) Applicant: Genetesis, Inc., Mason, OH (US)

(72) Inventors: Raj Muchhala, Mason, OH (US); Emmanuel T. Setegn, Mason, OH (US); Benjamin Donaldson Moore, Mason, OH (US)

(73) Assignee: Genetesis, Inc., Mason, OH (US)

( * ) Notice: Subject to any disclaimer, the term of this patent is extended or adjusted under 35 U.S.C. 154(b) by 38 days.

This patent is subject to a terminal disclaimer.

(21) Appl. No.: 17/972,889

(22) Filed: Oct. 25, 2022

(65) Prior Publication Data

US 2023/0181077 A1 Jun. 15, 2023

Related U.S. Application Data

(63) Continuation of application No. 15/985,512, filed on May 21, 2018, now Pat. No. 11,517,235.

(Continued)

(51) Int. Cl.
*A61B 5/243* (2021.01)
*A61B 5/00* (2006.01)
(Continued)

(52) U.S. Cl.
CPC ............... *A61B 5/243* (2021.01); *A61B 5/24* (2021.01); *A61B 5/245* (2021.01);
(Continued)

(58) Field of Classification Search
CPC . A61B 5/04007; A61B 5/04008; A61B 5/026; A61B 5/4094; A61B 2562/18;
(Continued)

(56) References Cited

U.S. PATENT DOCUMENTS

| | | |
|---|---|---|
| 4,600,886 A | 7/1986 | Jensen |
| 5,122,744 A | 6/1992 | Koch |

(Continued)

FOREIGN PATENT DOCUMENTS

| | | |
|---|---|---|
| CN | 1259025 A | 7/2000 |
| CN | 1471374 A | 1/2004 |

(Continued)

OTHER PUBLICATIONS

Haberkorn et al., Pseudo current density maps of electrophysiological heart, nerve or brain function and their physical basis, BioMagnetic Research and Technology vol. 4, Article No. 5 (2006) (Year: 2006).*

(Continued)

*Primary Examiner* — John D Li
(74) *Attorney, Agent, or Firm* — Goodwin Procter LLP

(57) ABSTRACT

Abnormalities in electromagnetic fields in the heart, brain, and stomach, among other organs and tissues of the human body, can be indicative of serious health conditions. Described herein are methods, software, systems and devices for detecting the presence of an abnormality in an organ or tissue of a subject by analysis of the electromagnetic fields generated by the organ or tissue.

21 Claims, 16 Drawing Sheets
(8 of 16 Drawing Sheet(s) Filed in Color)

Related U.S. Application Data

(60) Provisional application No. 62/509,433, filed on May 22, 2017.

(51) Int. Cl.

| | | |
|---|---|---|
| *A61B 5/026* | (2006.01) | |
| *A61B 5/24* | (2021.01) | |
| *A61B 5/245* | (2021.01) | |
| *G01R 33/035* | (2006.01) | |
| *G01R 33/12* | (2006.01) | |
| *G06N 3/044* | (2023.01) | |
| *G06N 3/045* | (2023.01) | |
| *G06N 3/047* | (2023.01) | |
| *G06N 3/084* | (2023.01) | |
| *G06N 3/088* | (2023.01) | |
| *G06N 20/00* | (2019.01) | |
| *G16H 40/63* | (2018.01) | |
| *G16H 50/20* | (2018.01) | |
| *G16H 50/30* | (2018.01) | |
| *G06N 5/01* | (2023.01) | |
| *G06N 20/10* | (2019.01) | |
| *G06N 20/20* | (2019.01) | |

(52) U.S. Cl.
CPC ..... *G01R 33/0354* (2013.01); *G01R 33/1238* (2013.01); *G06N 3/044* (2023.01); *G06N 3/045* (2023.01); *G06N 3/047* (2023.01); *G06N 3/084* (2013.01); *G06N 3/088* (2013.01); *G06N 20/00* (2019.01); *A61B 5/026* (2013.01); *A61B 5/4094* (2013.01); *A61B 2562/18* (2013.01); *G06N 5/01* (2023.01); *G06N 20/10* (2019.01); *G06N 20/20* (2019.01); *G16H 40/63* (2018.01); *G16H 50/20* (2018.01); *G16H 50/30* (2018.01)

(58) Field of Classification Search
CPC ...... A61B 5/7267; G06N 20/00; G06N 20/10; G06N 20/20; G06N 3/0445; G06N 3/0454; G06N 3/0472; G06N 3/084; G06N 3/088; G06N 5/003; G01R 33/0354; G01R 33/1238; G16H 40/63
See application file for complete search history.

(56) References Cited

U.S. PATENT DOCUMENTS

| | | |
|---|---|---|
| 5,697,369 A | 12/1997 | Long, Jr. et al. |
| 5,715,821 A | 2/1998 | Faupel |
| 5,771,894 A | 6/1998 | Richards et al. |
| 5,785,653 A | 7/1998 | Kiyuna et al. |
| 6,195,576 B1 | 2/2001 | John |
| 6,230,037 B1 | 5/2001 | Tsukada et al. |
| 6,339,328 B1 | 1/2002 | Keene et al. |
| 6,385,479 B1 | 5/2002 | Sibbitt et al. |
| 6,390,098 B1 | 5/2002 | LaFontaine et al. |
| 6,522,908 B1 * | 2/2003 | Miyashita ............ A61B 5/0064 600/409 |
| 6,597,940 B2 | 7/2003 | Bishop et al. |
| 7,270,670 B1 | 9/2007 | Yencho |
| 7,395,107 B2 | 7/2008 | Ishiyama et al. |
| 7,599,728 B2 | 10/2009 | Feenan |
| 7,634,360 B2 | 12/2009 | Davalos et al. |
| 7,646,274 B2 | 1/2010 | Rapoport |
| 7,801,591 B1 | 9/2010 | Shusterman |
| 7,805,179 B2 | 9/2010 | Horng et al. |
| 8,060,179 B1 | 11/2011 | Flynn |
| 8,172,776 B2 | 5/2012 | Browne |
| 8,310,230 B2 | 11/2012 | Haensch et al. |
| 8,315,713 B2 | 11/2012 | Burnes et al. |
| 8,323,188 B2 | 12/2012 | Tran |
| 8,553,956 B2 | 10/2013 | Wu et al. |
| 9,433,363 B1 | 9/2016 | Erasala et al. |
| 9,788,741 B2 | 10/2017 | Erasala et al. |
| 10,076,256 B2 | 9/2018 | Erasala et al. |
| 10,140,421 B1 | 11/2018 | Bernard et al. |
| 10,602,940 B1 | 3/2020 | Muchhala et al. |
| 10,925,502 B2 | 2/2021 | Muchhala et al. |
| 10,952,628 B2 | 3/2021 | Erasala et al. |
| 11,134,877 B2 | 10/2021 | Erasala et al. |
| 11,375,935 B2 | 7/2022 | Muchhala et al. |
| 11,517,235 B2 | 12/2022 | Muchhala et al. |
| 11,585,869 B2 | 2/2023 | Setegn et al. |
| 2001/0029329 A1 | 10/2001 | Avrin et al. |
| 2002/0045813 A1 | 4/2002 | Suzuki et al. |
| 2002/0077537 A1 | 6/2002 | Avrin et al. |
| 2002/0103428 A1 | 8/2002 | deCharms |
| 2003/0018277 A1 | 1/2003 | He |
| 2003/0097056 A1 | 5/2003 | Suzuki et al. |
| 2003/0135128 A1 | 7/2003 | Suffin et al. |
| 2003/0149354 A1 | 8/2003 | Bakharev |
| 2004/0039291 A1 | 2/2004 | Nakai et al. |
| 2004/0106863 A1 | 6/2004 | Seki et al. |
| 2004/0232912 A1 | 11/2004 | Tsukamoto et al. |
| 2004/0243022 A1 | 12/2004 | Carney et al. |
| 2004/0254443 A1 | 12/2004 | Gott et al. |
| 2005/0020903 A1 | 1/2005 | Krishnan et al. |
| 2005/0096531 A1 | 5/2005 | Oonuma et al. |
| 2005/0148844 A1 | 7/2005 | Ogata et al. |
| 2005/0152703 A1 | 7/2005 | Ogawa |
| 2005/0192502 A1 | 9/2005 | Ishiyama et al. |
| 2005/0285492 A1 | 12/2005 | Hu et al. |
| 2006/0122525 A1 | 6/2006 | Shusterman |
| 2006/0149354 A1 | 7/2006 | Shanley et al. |
| 2006/0234304 A1 | 10/2006 | Amann-Zalan et al. |
| 2006/0277075 A1 | 12/2006 | Salwan |
| 2007/0120563 A1 | 5/2007 | Kawabata et al. |
| 2007/0167723 A1 | 7/2007 | Park et al. |
| 2007/0167846 A1 | 7/2007 | Sternickel et al. |
| 2007/0213600 A1 | 9/2007 | John et al. |
| 2007/0276270 A1 | 11/2007 | Tran |
| 2008/0033312 A1 | 2/2008 | Nakai et al. |
| 2008/0091118 A1 | 4/2008 | Georgopoulos |
| 2008/0108504 A1 | 5/2008 | Matsui et al. |
| 2008/0137927 A1 | 6/2008 | Altmann et al. |
| 2008/0306359 A1 | 12/2008 | Zdeblick et al. |
| 2009/0149736 A1 | 6/2009 | Skidmore et al. |
| 2009/0172773 A1 | 7/2009 | Moore |
| 2009/0177107 A1 | 7/2009 | Guion-Johnson |
| 2009/0281413 A1 | 11/2009 | Boyden et al. |
| 2009/0295385 A1 | 12/2009 | Brazdeikis et al. |
| 2009/0295386 A1 | 12/2009 | Sato et al. |
| 2009/0299200 A1 | 12/2009 | Eggenberger et al. |
| 2010/0004708 A1 | 1/2010 | Jahns et al. |
| 2010/0036269 A1 | 2/2010 | Ferren et al. |
| 2010/0090697 A1 | 4/2010 | Savukov et al. |
| 2010/0249620 A1 | 9/2010 | Cho |
| 2011/0041520 A1 | 2/2011 | Erne et al. |
| 2011/0047105 A1 | 2/2011 | Sternickel et al. |
| 2011/0119212 A1 | 5/2011 | De Bruin et al. |
| 2011/0152703 A1 | 6/2011 | Zuckerman et al. |
| 2011/0160546 A1 | 6/2011 | Madsen |
| 2011/0224962 A1 | 9/2011 | Goldberger et al. |
| 2011/0275949 A1 | 11/2011 | Harlev et al. |
| 2011/0306896 A1 | 12/2011 | Altmann |
| 2011/0313274 A1 | 12/2011 | Subbarao |
| 2012/0197145 A1 | 8/2012 | Wu et al. |
| 2012/0219195 A1 | 8/2012 | Wu et al. |
| 2012/0239560 A1 | 9/2012 | Pourfallah et al. |
| 2012/0284332 A1 | 11/2012 | Pradeep et al. |
| 2012/0289954 A1 | 11/2012 | Lam |
| 2012/0310107 A1 | 12/2012 | Doidge et al. |
| 2013/0038325 A1 | 2/2013 | Okada |
| 2013/0057385 A1 | 3/2013 | Murakami et al. |
| 2013/0072780 A1 | 3/2013 | Espy et al. |
| 2013/0079622 A1 | 3/2013 | Wu et al. |
| 2013/0096394 A1 | 4/2013 | Gupta et al. |
| 2013/0132109 A1 | 5/2013 | Mruthyunjaya et al. |
| 2013/0184569 A1 | 7/2013 | Strommer et al. |

(56) References Cited

U.S. PATENT DOCUMENTS

| | | |
|---|---|---|
| 2013/0203061 A1* | 8/2013 | Kuslich .............. G01N 33/5076 |
| | | 435/6.12 |
| 2013/0241929 A1 | 9/2013 | Massarwa et al. |
| 2013/0317337 A1 | 11/2013 | Wu et al. |
| 2013/0324832 A1 | 12/2013 | Wu et al. |
| 2014/0107511 A1 | 4/2014 | Banet et al. |
| 2014/0171757 A1 | 6/2014 | Kawato et al. |
| 2014/0308930 A1 | 10/2014 | Tran |
| 2014/0323848 A1 | 10/2014 | He et al. |
| 2014/0343396 A1 | 11/2014 | Sternickel et al. |
| 2014/0343397 A1 | 11/2014 | Kim et al. |
| 2014/0379269 A1 | 12/2014 | Schmitt |
| 2015/0011844 A1 | 1/2015 | Paradis |
| 2015/0011862 A1 | 1/2015 | Chaykovskyy |
| 2015/0080703 A1 | 3/2015 | Reiman |
| 2015/0150475 A1 | 6/2015 | Varcoe |
| 2015/0212166 A1 | 7/2015 | Kandori et al. |
| 2015/0366546 A1 | 12/2015 | Kamen et al. |
| 2016/0007879 A1 | 1/2016 | Gonzalez et al. |
| 2016/0044841 A1 | 2/2016 | Chamberlain |
| 2016/0066860 A1 | 3/2016 | Sternickel et al. |
| 2016/0120432 A1 | 5/2016 | Sridhar et al. |
| 2016/0131723 A1 | 5/2016 | Nagasaka |
| 2016/0135706 A1* | 5/2016 | Sullivan ................. A61B 7/003 |
| | | 600/509 |
| 2016/0154072 A1 | 6/2016 | Nagasaka et al. |
| 2016/0154073 A1 | 6/2016 | Nagasaka et al. |
| 2016/0287166 A1 | 10/2016 | Tran |
| 2017/0007148 A1 | 1/2017 | Kaditz et al. |
| 2017/0027498 A1 | 2/2017 | Larson et al. |
| 2017/0032922 A1 | 2/2017 | Champeaux et al. |
| 2017/0053082 A1 | 2/2017 | Pereira et al. |
| 2017/0071499 A1 | 3/2017 | Nebuya et al. |
| 2017/0135633 A1 | 5/2017 | Connor |
| 2017/0173262 A1 | 6/2017 | Veltz |
| 2017/0202509 A1 | 7/2017 | Sanderson et al. |
| 2017/0258348 A1 | 9/2017 | Erasala et al. |
| 2017/0329922 A1 | 11/2017 | Eberting et al. |
| 2017/0332918 A1 | 11/2017 | Keane |
| 2017/0352158 A1 | 12/2017 | Raina |
| 2018/0000371 A1 | 1/2018 | Gupta et al. |
| 2018/0064400 A1 | 3/2018 | Chbat et al. |
| 2018/0070841 A1 | 3/2018 | Honore et al. |
| 2018/0078146 A1 | 3/2018 | Shadforth et al. |
| 2018/0078767 A1 | 3/2018 | Rapoport et al. |
| 2018/0089531 A1 | 3/2018 | Geva et al. |
| 2018/0093092 A1 | 4/2018 | Howard |
| 2018/0128886 A1 | 5/2018 | Nagasaka |
| 2018/0158552 A1 | 6/2018 | Liu et al. |
| 2018/0224508 A1 | 8/2018 | Kelly et al. |
| 2018/0235470 A1 | 8/2018 | Johnson et al. |
| 2018/0236255 A1 | 8/2018 | Etkin |
| 2018/0263561 A1 | 9/2018 | Jones |
| 2018/0322351 A1 | 11/2018 | Shaker |
| 2018/0333063 A1 | 11/2018 | Muchhala et al. |
| 2018/0333104 A1* | 11/2018 | Sitek ...................... A61B 5/364 |
| 2019/0018080 A1 | 1/2019 | Marauska et al. |
| 2019/0021621 A1 | 1/2019 | Erasala et al. |
| 2019/0046059 A1 | 2/2019 | Erasala et al. |
| 2019/0108833 A1 | 4/2019 | van den Oord et al. |
| 2019/0117164 A1 | 4/2019 | Gupta et al. |
| 2019/0167136 A1 | 6/2019 | Kawabata et al. |
| 2019/0192021 A1 | 6/2019 | Kim et al. |
| 2019/0336231 A1 | 11/2019 | Kidd et al. |
| 2019/0365266 A1 | 12/2019 | Varcoe et al. |
| 2019/0368191 A1 | 12/2019 | Shibuya |
| 2020/0081079 A1 | 3/2020 | Khitun |
| 2020/0152330 A1 | 5/2020 | Anushiravani et al. |
| 2020/0170528 A1 | 6/2020 | Erasala et al. |
| 2020/0187802 A1 | 6/2020 | Muchhala et al. |
| 2020/0211713 A1 | 7/2020 | Shadforth et al. |
| 2020/0258627 A1 | 8/2020 | Setegn et al. |
| 2020/0388287 A1 | 12/2020 | Anushiravani et al. |
| 2021/0027893 A1 | 1/2021 | Nematihosseinabadi et al. |
| 2021/0325482 A1 | 10/2021 | Setegn et al. |
| 2022/0015677 A1 | 1/2022 | Erasala et al. |
| 2023/0204688 A1 | 6/2023 | Setegn et al. |

FOREIGN PATENT DOCUMENTS

| | | | |
|---|---|---|---|
| CN | 101926646 A | 12/2010 | |
| CN | 102355859 A | 2/2012 | |
| CN | 104188650 A | 12/2014 | |
| CN | 204133457 U | 2/2015 | |
| CN | 104620123 A | 5/2015 | |
| CN | 113316412 A | 8/2021 | |
| EP | 1302160 A1 | 4/2003 | |
| EP | 3077037 A1 | 10/2016 | |
| EP | 3308703 A1 * | 4/2018 | ......... A61B 5/04007 |
| EP | 3883457 A1 | 9/2021 | |
| GB | 2179455 A | 3/1987 | |
| JP | H04319334 A | 11/1992 | |
| JP | 2000254108 A | 9/2000 | |
| JP | 2002028144 A | 1/2002 | |
| JP | 2002355229 A | 12/2002 | |
| JP | 2004041739 A | 2/2004 | |
| JP | 2004237083 A | 8/2004 | |
| JP | 2004337478 A | 12/2004 | |
| JP | 2005080951 A | 3/2005 | |
| JP | 2007117669 A | 5/2007 | |
| JP | 2008307141 A | 12/2008 | |
| JP | 2014525787 A | 10/2014 | |
| JP | 2015091359 A | 5/2015 | |
| JP | 2016101264 A | 6/2016 | |
| JP | 2016530019 A | 9/2016 | |
| KR | 20180046432 A | 5/2018 | |
| WO | WO-1998049938 A1 | 11/1998 | |
| WO | WO-2002017769 A2 | 3/2002 | |
| WO | WO-2005002313 A2 | 1/2005 | |
| WO | WO-2008005513 A2 | 1/2008 | |
| WO | WO-2011116229 A2 | 9/2011 | |
| WO | WO-2013011515 A1 | 1/2013 | |
| WO | WO-2014011940 A2 | 1/2014 | |
| WO | WO-2014152110 A1 | 9/2014 | |
| WO | WO-2015033244 A1 | 3/2015 | |
| WO | WO-2015085011 A1 | 6/2015 | |
| WO | WO-2015129756 A1 | 9/2015 | |
| WO | WO-2016205731 A1 | 12/2016 | |
| WO | WO-2018069287 A1 | 4/2018 | |
| WO | WO-2018217655 A1 | 11/2018 | |
| WO | WO-2019032857 A1 | 2/2019 | |
| WO | WO-2020106284 A1 | 5/2020 | |
| WO | WO-2020163593 A1 | 8/2020 | |
| WO | WO-20210242868 A1 | 12/2021 | |
| WO | WO-2022178314 A1 | 8/2022 | |
| WO | WO-2023168392 A2 | 9/2023 | |

OTHER PUBLICATIONS

Boussaa, et al. ECG Signals Classification Using MFCC Coefficients and ANN Classifier, 2nd International Conference on Electrical and Information Technologies ICEIT 2016.
Japanese Patent Application No. 2019-564526 Notice of Reasons for Refusal dated Jan. 25, 2023.
Japanese Patent Application No. 2019-564526 Notice of Reasons for Refusal dated Mar. 22, 2022.
Lyons, J. Mel Frequency Cepstral Coefficient (MFCC) tutorial. Retrieved from <http://practicalcryptography.com/miscellaneous/machine-learning/guide-mel-frequency-cepstral-coefficients-mfccs/> on Jun. 6, 2017.
U.S. Appl. No. 15/601,417 Non-Final Office Action Mailed Sep. 27, 2017.
U.S. Appl. No. 15/985,512 Notice of Allowance dated Jul. 27, 2022.
Amsterdam, E.A., et al., Testing of low-risk patients presenting to the emergency department with chest pain: a scientific statement from the American Heart Association, Circulation, 122(17): 1756-1776 (2010).
Arbab-Zadeh, A., Stress testing and non-invasive coronary angiography in patients with suspected coronary artery disease: time for a new paradigm, Heart Int, 7(1): e2 (2012).

(56) References Cited

OTHER PUBLICATIONS

CN201880048311.1 Chinese Office Action dated Mar. 8, 2022.
EP Application No. 16812571.4 94(3) Communication dated Aug. 30, 2021.
EP Application No. 18940759.6 Extended European Search Report dated Jun. 3, 2022.
EP18805647.7 Extended European Search Report dated Dec. 17, 2020.
EP18844754.4 Extended European Search Report dated Mar. 12, 2021.
Fenici, R., et al., Clinical validation of machine learning for automatic analysis of multichannel magnetocardiography, Proceedings of the Third International Conference on Functional Imaging and Modeling of the Heart (FIMH): Lecture Notes in Computer Science Book Series (LNTCS), vol. 3504: 143-152 (2005). doi: 10.1007/11494621_15.
Haberkorn, W., et al., Pseudo current density maps of electrophysiological heart, nerve or brain function and their physical basis, Biomagn Res Technol, 4:5 (2006).
He, K., et al., A high-performance compact magnetic shield for optically pumped magnetometer- based magnetoencephalography, Rev Sci Instrum, 90(6): 064102, pp. 1-8 (2019).
Heron, M., et al., Deaths: Leading Causes for 2014, Natl Vital Stat Rep, 65(5): 1-96 (2016).
Jurkko, R., et al., Non-invasive detection of conduction pathways to left atrium using magnetocardiography: validation by intra-cardiac electroanatomic mapping, Eurospace, 11(2): 169-177 (2009).
Killman, R., et al., Localisation of myocardial ischaemia from the magnetocardiogram using current density reconstruction method: computer simulation study, Med Biol Eng Comput, 33(5): 643-651 (1995).
Liao, Y., et al., Denoising of Magnetocardiography Based on Improved Variational Mode Decomposition and Interval Thresholding Method, Symmetry, 10(7): 269 (2018).
Moseley, M.G., et al., Emergency department observation units and the older patient, Clin Geriatr Med, 29(1): 71-89 (2013).
PCT/US2016/038209 International Preliminary Report on Patentability mailed Dec. 28, 2017.
PCT/US2016/038209 International Search Report and Written Opinion mailed Sep. 14, 2016.
PCT/US2018/033719 International Preliminary Report on Patentability mailed Nov. 26, 2019.
PCT/US2018/033719 International Search Report and Written Opinion mailed Aug. 27, 2018.
PCT/US2018/046055 International Preliminary Report on Patentability mailed Feb. 11, 2020.
PCT/US2018/046055 International Search Report and Written Opinion mailed Oct. 17, 2018.
PCT/US2018/062113 International Search Report and Written Opinion mailed Jan. 31, 2019.
PCT/US2020/017010 International Preliminary Report on Patentability dated Aug. 10, 2021.
PCT/US2020/017010 International Search Report and Written Opinion mailed May 4, 2020.
PCT/US2021/034269 International Preliminary Report on Patentability mailed Nov. 17, 2022.
PCT/US2021/034269 International Search Report and Written Opinion mailed Sep. 8, 2021.
PCT/US2022/017085 International Preliminary Report on Patentability dated Aug. 22, 2023.
PCT/US2022/017085 International Search Report and Written Opinion mailed Mar. 14, 2022.
PCT/US2023/063666 International Search Report and Written Opinion mailed Sep. 5, 2023.
Reinhardt, S.W., et al., Noninvasive Cardiac Testing vs Clinical Evaluation Alone in Acute Chest Pain: A Secondary Analysis of the ROMICAT-II Randomized Clinical Trial, JAMA Intern Med, 178(2): 212-219 (2018).
Sasada, I., et al., Effective shielding for low-level magnetic fields, J Appl Phys, 64(10): 5696-5698 (1988).
Tantimongcolwat, T., et al., Identification of ischemic heart disease via machine learning analysis on magnetocardiograms, Comput Biol Med, 38(7): 817-825 (2008).
U.S. Appl. No. 16/197,264 Office Action mailed Feb. 5, 2019.
U.S. Appl. No. 16/197,264 Office Action mailed Jul. 31, 2019.
U.S. Appl. No. 16/775,630 Office Action mailed Apr. 23, 2020.
U.S. Appl. No. 17/129,585 Office Action mailed Apr. 16, 2021.
U.S. Appl. No. 17/129,585 Office Action mailed Aug. 24, 2021.
U.S. Appl. No. 17/830,879 Office Action mailed Mar. 31, 2023.
U.S. Appl. No. 14/941,455 Notice of Allowance mailed Jul. 7, 2016.
U.S. Appl. No. 14/941,455 Office Action mailed Apr. 4, 2016.
U.S. Appl. No. 14/941,455 Office Action mailed Feb. 17, 2016.
U.S. Appl. No. 15/220,982 Notice of Allowance mailed May 9, 2017.
U.S. Appl. No. 15/220,982 Office Action mailed Dec. 27, 2016.
U.S. Appl. No. 15/607,053 Notice of Allowance mailed May 15, 2018.
U.S. Appl. No. 15/607,053 Office Action mailed Dec. 22, 2017.
U.S. Appl. No. 15/673,067 Office Action dated Feb. 5, 2021.
U.S. Appl. No. 15/673,067 Office Action dated May 11, 2020.
U.S. Appl. No. 15/673,067 Office Action dated Oct. 13, 2020.
U.S. Appl. No. 15/985,512 Office Action dated Feb. 11, 2022.
U.S. Appl. No. 15/985,512 Office Action dated Feb. 12, 2021.
U.S. Appl. No. 15/985,512 Office Action dated Sep. 21, 2021.
U.S. Appl. No. 15/985,512 Office Action dated Sep. 25, 2020.
U.S. Appl. No. 16/104,528 Office Action mailed Feb. 26, 2020.
U.S. Appl. No. 16/104,528 Office Action mailed Nov. 7, 2019.
U.S. Appl. No. 16/271,705 Office Action dated Aug. 20, 2020.
U.S. Appl. No. 16/271,705 Office Action dated Jan. 9, 2020.
U.S. Appl. No. 16/271,705 Office Action dated Jul. 1, 2019.
U.S. Appl. No. 16/271,705 Office Action dated May 1, 2020.
U.S. Appl. No. 16/636,860 Office Action dated Feb. 28, 2024.
U.S. Appl. No. 16/636,860 Office Action dated Jul. 18, 2022.
U.S. Appl. No. 16/636,860 Office Action dated Nov. 9, 2023.
U.S. Appl. No. 17/181,095 Office Action dated Jun. 3, 2021.
U.S. Appl. No. 17/181,095 Office Action dated Mar. 29, 2022.
U.S. Appl. No. 17/181,095 Office Action dated Sep. 29, 2021.
U.S. Appl. No. 17/403,029 Office Action dated Dec. 7, 2022.
U.S. Appl. No. 17/403,029 Office Action dated Oct. 6, 2023.
U.S. Appl. No. 17/403,029 Office Action mailed Jan. 29, 2024.
Watanabe, S., et al., Magnetocardiography in Early Detection of Electromagnetic Abnormality in Ischemic Heart Disease, J Arrhythmia, 24(1): 4-17 (2008).
U.S. Appl. No. 14/941,455, filed Nov. 13, 2015, U.S. Pat. No. 9,433,363, Sep. 6, 2016, Issued.
U.S. Appl. No. 15/220,982, filed Jul. 27, 2016, U.S. Pat. No. 9,788,741, Oct. 17, 2017, Issued.
U.S. Appl. No. 15/607,053, filed May 26, 2017, U.S. Pat. No. 10,076,256, Sep. 18, 2018, Issued.
U.S. Appl. No. 16/104,528, filed Aug. 17, 2018, U.S. Pat. No. 10,952,628, Mar. 23, 2021, Issued.
U.S. Appl. No. 17/171,118, filed Feb. 9, 2021, U.S. Pat. No. 11,957,470, Apr. 16, 2024, Issued.
U.S. Appl. No. 18/607,151, filed Mar. 15, 2024, Pending.
U.S. Appl. No. 15/601,417, filed May 22, 2017, Abandoned.
U.S. Appl. No. 15/985,512, filed May 21, 2018, U.S. Pat. No. 11,517,235, Dec. 6, 2022, Issued.
U.S. Appl. No. 15/673,067, filed Aug. 9, 2017, U.S. Pat. No. 11,134,877, Oct. 5, 2021, Issued.
U.S. Appl. No. 16/636,860, filed Feb. 5, 2020, Pending.
U.S. Appl. No. 17/403,029, filed Aug. 16, 2021, Pending.
U.S. Appl. No. 16/197,264, filed Nov. 20, 2018, U.S. Pat. No. 10,602,940, Mar. 31, 2020, Issued.
U.S. Appl. No. 16/775,630, filed Jan. 29, 2020, U.S. Pat. No. 10,925,502, Feb. 23, 2021, Issued.
U.S. Appl. No. 17/129,585, filed Dec. 21, 2020, U.S. Pat. No. 11,375,935, Jul. 5, 2022, Issued.
U.S. Appl. No. 17/830,879, filed Jun. 2, 2022, U.S. Pat. No. 11,903,714, Feb. 20, 2021, Issued.
U.S. Appl. No. 18/411,247, filed Jan. 12, 2024, Pending.
U.S. Appl. No. 16/271,705, filed Feb. 8, 2019, Abandoned.
U.S. Appl. No. 18/084,983, filed Dec. 20, 2022, Pending.

(56) References Cited

OTHER PUBLICATIONS

U.S. Appl. No. 17/181,095, filed Feb. 22, 2021, U.S. Pat. No. 11,585,869, Feb. 21, 2023, Issued.
U.S. Appl. No. 17/987,232, filed Nov. 15, 2022, Pending.
U.S. Appl. No. 18/116,965, filed Mar. 3, 2023, Pending.

* cited by examiner

MACHINE DIFFERENTIATION OF ABNORMALITIES IN BIOELECTROMAGNETIC FIELDS

CROSS-REFERENCE

This application is a continuation of U.S. application Ser. No. 15/985,512, filed May 21, 2018, which claims the benefit of U.S. Provisional Application No. 62/509,433, filed May 22, 2017, each of which is incorporated by reference herein in its entirety.

BACKGROUND

Human and animal tissue is associated with an electromagnetic field (EMF) due to electrical currents passing through said tissue. For example, Magnetocardiography (MCG) can be used to detect an EMF associated with a heart. For example, Magnetoencephalography (MEG) can be used to detect an EMF associated with a brain. For example, Magnetogastrography (MGG) can be used to detect an EMF associated with a stomach. Abnormalities in such electromagnetic fields can be indicative of serious health conditions.

SUMMARY

Abnormalities in the EMF of the heart, brain, and stomach, among other organs and tissue of the human body, can be indicative of serious health conditions. Described herein are devices, systems, methods, and software for analyzing the EMF and generating an output associated with a health condition of the individual based on the EMF generated by the organ or tissue.

In some embodiments of devices, systems, methods, and software described herein, analysis of an EMF is achieved by utilizing a machine learning software module to identify abnormalities in a subject's organs or tissues.

In some embodiments, a machine learning software module is trained using EMF data and data relating to an individual including their records and data relating to the organs and/or tissue in the body of the individual. Abnormality data includes the presence or absence of an abnormality within an organ or tissue, and said abnormalities are identified along with any known resulting or associated disease, disorder or condition. Data relating to an individual includes demographic data, medical image data, clinical data (e.g. from a health record, including an Electronic Health Record), encoded data, and encoded features, or metrics derived from an electromagnetic field EMF data includes EMF measurements and simulations of EMF measurements. The machine learning software module described herein, in some embodiments, is trained on both EMF data and the corresponding abnormality data (i.e. that corresponds to an EMF data), such that the machine learning software module is able to analyze new EMF data and determine whether an abnormality is present based on training. Furthermore, the machine learning software module may determine a condition associated with the detected abnormality.

Described herein are methods, software, systems and devices for detecting the presence of an abnormality in an organ or tissue of a subject by analysis of the electromagnetic fields generated by the organ or tissue. In some embodiments, EMF data is used to generate one or more of a medical image, clinical data, and encoded data. In these embodiments, medical image data, clinical data, encoded data and/or other features or metrics derived from the EMF data are used as inputs to train a machine learning algorithm which is configured to identify a presence of an abnormality in an individual. Said abnormality may be related to an organ from which an EMF is sensed or other organs or systems in an individual. In some embodiments, a machine learning algorithm is configured to determine or predict an abnormality score for an individual.

Described herein are methods, software, systems and devices for diagnosing the presence of an abnormality in an individual comprising: sensing an electromagnetic field data associated with the individual using an electromagnetic field sensor, generating medical image data and/or clinical data and/or encoded data and/or features or metrics derived from the said data using the EMF data, constructing a hypothesis function in the training phase using a known patient database of one or more medical image and/or clinical data and/or encoded data from the EMF measurements and/or any features or metrics computed from the above said data, and predicting probability of an abnormality in an unknown medical image and/or clinical data and/or encoded data from the EMF measurements and/or any features or metrics computed from the above said data of one or more patients using the constructed hypothesis function from the training phase.

Described herein are methods, software, systems and devices for diagnosing the presence of an abnormality in an individual comprising: sensing an electromagnetic field data associated with the individual using an electromagnetic field sensor, generating an analysis of the electromagnetic field data using a machine learning algorithm, and determining the presence of an abnormality in the individual based on the analysis of the electromagnetic field data.

Described herein is a method for diagnosing a presence of an abnormality in an individual comprising: sensing an electromagnetic field data associated with the individual using an electromagnetic field sensor, generating medical image data and/or clinical data and/or encoded data and/or features or metrics derived from the said data using the EMF data, constructing a hypothesis function in the training phase using a known patient database of one or more medical image and/or clinical data and/or encoded data from the EMF measurements and/or any features or metrics computed from the above said data, and predicting probability of an abnormality in an unknown medical image and/or clinical data and/or encoded data from the EMF measurements and/or any features or metrics computed from the above said data of one or more patients using the constructed hypothesis function from the training phase. In some embodiments, the abnormality comprises a cardiac abnormality. In some embodiments, the abnormality comprises ischemia. In some embodiments, the machine learning algorithm comprises a neural network. In some embodiments, the machine learning algorithm is trained using an input generated from a computer simulation.

Described herein is a method for diagnosing a presence of an abnormality in an individual comprising: sensing an electromagnetic data associated with the individual using an electromagnetic sensor; generating an analysis of the electromagnetic data using a machine learning algorithm; and determining the presence of an abnormality in the individual based on the analysis of the electromagnetic data. In some embodiments, the abnormality comprises a cardiac abnormality. In some embodiments, the abnormality comprises ischemia. In some embodiments, the machine learning algorithm comprises a neural network. In some embodiments, the machine learning algorithm is trained using an input generated from a computer simulation. In some embodiments, the method comprises filtering of the electromagnetic data. In some embodiments, the filtering the electromagnetic data comprises generating a cepstral coefficient using the electromagnetic data. In some embodiments, generating the cepstral coefficient comprises: (a) segmenting the electromagnetic data into one or more segments; (b) calculating a periodogram estimate of a power spectrum for each of the one or more segments; (c) calculating a sum of each of the periodogram estimates; (d) taking a logarithm of each of the sums; (e) calculating a Discrete Cosine Transform (DCT) for each of the logarithms thereby generating the cepstral coefficient for each of the one or more segments. In some embodiments, the method comprises discarding at least one cepstral coefficient. In some embodiments, an input to the machine learning algorithm comprises at least one cepstral coefficient.

Described herein is a computer-implemented system comprising: an electromagnetic sensor configured to sense an electromagnetic data associated with an individual; and a computer program including instructions executable by the digital processing device to determine the presence of an abnormality in said individual, the computer program comprising: a software module configured to receive said electromagnetic data; a software module comprising a machine learning algorithm configured to analyze said electromagnetic data and determine said presence of said abnormality. In some embodiments, the abnormality comprises a cardiac abnormality. In some embodiments, the abnormality comprises ischemia. In some embodiments, the machine learning algorithm comprises a neural network. In some embodiments, the machine learning algorithm is trained using an input generated from a computer simulation. In some embodiments, the system comprises a software module configured to filter the electromagnetic data. In some embodiments, the software module configured to filter the electromagnetic data generates a cepstral coefficient using the electromagnetic data. In some embodiments, generating the cepstral coefficient comprises: (a) segmenting the electromagnetic data into one or more segments; (b) calculating a periodogram estimate of a power spectrum for each of the one or more segments; (c) calculating a sum of each of the periodogram estimates; (d) taking a logarithm of each of the sums; (e) calculating a Discrete Cosine Transform (DCT) for each of the logarithms thereby generating the cepstral coefficient for each of the one or more segments. In some embodiments, generating the cepstral coefficient further comprises discarding at least one cepstral coefficient. In some embodiments, input to the machine learning algorithm comprises at least one cepstral coefficient.

Described herein is a diagnostic device configured to determine a medical diagnosis, said diagnostic device comprising: an electromagnetic field sensor configured to sense an electromagnetic field measurement associated with an individual; a processor operably coupled to the electromagnetic field sensor; and a non-transitory computer-readable storage media encoded with software comprising a trained machine learning software module, wherein said software is executable by the processor and causes the processor to: receive the electromagnetic field measurement from the electromagnetic field sensor; extract an extraction value from the electromagnetic field measurement using an extraction technique, wherein the trained machine learning software module determines the extraction technique that is used; associate the extraction value with one or more other values using a data association technique thereby generating a data association, wherein the trained machine learning software module determines the data association technique that is used; generate a hypothesis function based on the association; and determine a medical diagnosis for the individual based on the hypothesis function. In some embodiments, a sensor array and wherein the electromagnetic field sensor is positioned within the array. In some embodiments, the electromagnetic field sensor comprises an optically pumped magnetometer or a superconducting quantum interference device type sensor. In some embodiments, a housing containing said processor and wherein said electromagnetic sensor is hard-connected to said housing. In some embodiments, the trained machine learning software module has access to stored data comprising a plurality of electromagnetic field values sensed from a plurality of individuals within a population. In some embodiments, the stored data comprises a plurality of health data values associated with the plurality of individuals. In some embodiments, the trained machine learning software module has access to data used to train the trained machine learning software module. In some embodiments, the data used to train the trained machine learning software module comprises heart related data. In some embodiments, the heart related data comprises an electromagnetic field associated with a heart of the individual. In some embodiments, the data used to train the trained machine learning software module comprises brain related data. In some embodiments, wherein the brain related data comprises an electromagnetic field associated with a brain of the individual. In some embodiments, the extraction value comprises a segment of an electromagnetic waveform corresponding to the electromagnetic field measurement. In some embodiments, the electromagnetic field measurement is filtered. In some embodiments, the one or more data values comprise one or more of demographic data, medical image data, or clinical data associated with one or more individuals from a population. In some embodiments, the processor is further configured to translate the electromagnetic measurement to a waveform. In some embodiments, the processor is further configured to determine a therapy for treating the diagnosis. In some embodiments, the diagnosis comprises a heart-related diagnosis. In some embodiments, the diagnosis comprises a brain-related diagnosis.

Also described herein is a diagnostic method comprising: receiving an electromagnetic field measurement from an electromagnetic field sensor operably coupled to a sensing device comprising a processor and a trained machine learning software module; extracting, using the processor, an extraction value from the electromagnetic field measurement using an extraction technique, wherein a trained machine learning software module determines the extraction technique that is used; associating, using the processor, the extraction value with one or more other values using a data association technique thereby generating a data association, wherein the trained software module determines the data association technique that is used; generating, using the processor, a hypothesis function based on the association; and determining, using the processor, a medical diagnosis for the individual based on the hypothesis function.

In some embodiments, the sensing device comprises a sensor array and wherein the electromagnetic field sensor is positioned within the array. In some embodiments, the electromagnetic field sensor comprises an optically pumped magnetometer or a superconducting quantum interference device type sensor. In some embodiments, said electromagnetic sensor is hard-connected to said sensing device. In some embodiments, the method comprises accessing, by the trained machine learning software module, stored data comprising a plurality of electromagnetic field values sensed from a plurality of individuals within a population. In some embodiments, the stored data comprises a plurality of health data values associated with the plurality of individuals. In some embodiments, the method comprises accessing, by the trained machine learning software module, data used to train the trained machine learning software module. In some embodiments, the data used to train the trained machine learning software module comprises heart related data. In some embodiments, the heart related data comprises an electromagnetic field associated with a heart of the individual. In some embodiments, the data used to train the trained machine learning software module comprises brain related data. In some embodiments, the brain related data comprises an electromagnetic field associated with a brain of the individual. In some embodiments, the extraction value comprises a segment of an electromagnetic waveform corresponding to the electromagnetic field measurement. In some embodiments, the method comprises filtering the electromagnetic field measurement. In some embodiments, the one or more data values comprise one or more of demographic data, medical image data, or clinical data associated with one or more individuals from a population. In some embodiments, the processor is further configured to translate the electromagnetic field measurement to a waveform. In some embodiments, the processor is further configured to determine a therapy for treating the diagnosis. In some embodiments, the diagnosis comprises a heart-related diagnosis. In some embodiments, the diagnosis comprises a brain-related diagnosis.

BRIEF DESCRIPTION OF THE DRAWINGS

The patent or application file contains at least one drawing executed in color. Copies of this patent or patent application publication with color drawing(s) will be provided by the Office upon request and payment of the necessary fee. The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1A:
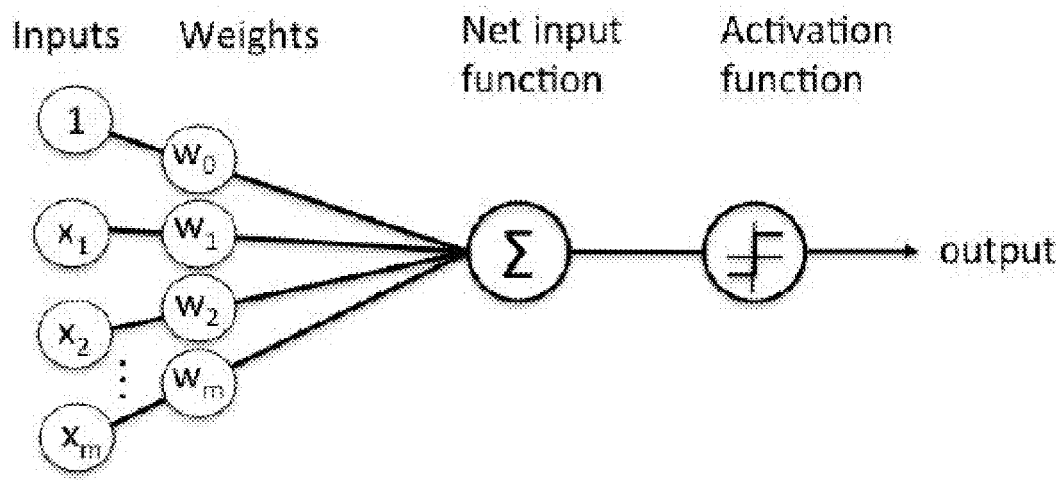
FIGS. 1A and 1B show schematic examples of neural network architecture in terms of flow of data within the neural network.

Described herein are devices, systems, methods, and software for determining an abnormality in an individual by sensing and analyzing EMF data associated with the individual.

Software Modules

Sensed EMF data, sensed by one or more EMF sensors, is received and analyzed by a software module comprising a machine learning software module.

In general, a software module as described herein comprises computer readable and executable code. In various embodiments, a software module comprises a file, a section of code, a programming object, a programming structure, or combinations thereof. In further various embodiments, a software module comprises a plurality of files, a plurality of sections of code, a plurality of programming objects, a plurality of programming structures, or combinations thereof. In various embodiments, the one or more software modules comprise, by way of non-limiting examples, a web application, a mobile application, and a standalone application. In some embodiments, software modules are in one computer program or application. In other embodiments, software modules are in more than one computer program or application. In some embodiments, software modules are hosted on one machine. In other embodiments, software modules are hosted on more than one machine. In further embodiments, software modules are hosted on cloud computing platforms. In some embodiments, software modules are hosted on one or more machines in one location. In other embodiments, software modules are hosted on one or more machines in more than one location.

In general, a machine learning software module as described herein is configured to receive data, analyze data, and generate an output. Non-limiting examples of an output generated by a machine learning software module include an abnormality, a disease state, an imbalance, a diagnosis, a prognosis, a prediction of a change in health status, a therapy suggestion including preventative therapy.

In some embodiments, a machine learning software module is configured to analyze sensed EMF data and generate a hypothesis function based on said sensed data. A hypothesis function generated by a machine learning software module as described herein, in some embodiments, is configured to determine a presence of an abnormality in an individual based on an EMF sensed from the individual and inputted into the machine learning software module. In some embodiments, a hypothesis function generated by a machine learning software module as described herein is configured to determine a prognosis for an individual based on an EMF sensed from the individual and inputted into the machine learning software module. In some embodiments, a hypothesis function is configured to determine a therapy suggestion for an individual based on an EMF sensed from the individual and inputted into the machine learning software module, wherein said therapy does one or more of treat an existing abnormality and prevent the onset of an abnormality. Analysis of EMF data by a machine learning software module, in some embodiments, comprises identification of an abnormality associated with sensed EMF data. For example, a machine learning algorithm as described herein may receive EMF data sensed from an individual and analyze said data to determine that said individual suffers from congestive heart failure.

Described herein are machine learning software modules configured to analyze EMF data using machine learning algorithms such as, for example, machine learning algorithms that utilize one or more neural networks. A neural network is a type of computational system that can learn the relationships between an input data set and a target data set. A neural network is a software representation of a human neural system (e.g. cognitive system), intended to capture "learning" and "generalization" abilities as used by a human. In some embodiments of the software module, the software module comprises a neural network comprising a convolutional neural network. Non limiting examples of structural components of embodiments of the machine learning software described herein include: (deep) convolutional neural networks, (deep) recurrent neural networks, (deep) dilated convolutional neural networks, (deep) fully connected neural networks, deep generative models, and (deep) (restricted) Boltzmann machines.

In some embodiments of the software applications and systems described herein, a machine learning software module comprises a recurrent neural network software module. A recurrent neural network software module is configured to receive sequential data as an input, such as consecutive EMF measurements, and the recurrent neural network software module updates an internal state at every time step.

In some embodiments, a machine learning software module comprises a supervised or unsupervised learning method such as, for example, SVM, random forests, clustering algorithms, gradient boosting, logistic regression, or decision trees.

In some embodiments, a machine learning software module comprises a neural network comprising a CNN, RNN, dilated CNN, fully connected neural networks, deep generative models and deep restricted Boltzmann machines.

Figure 1B:
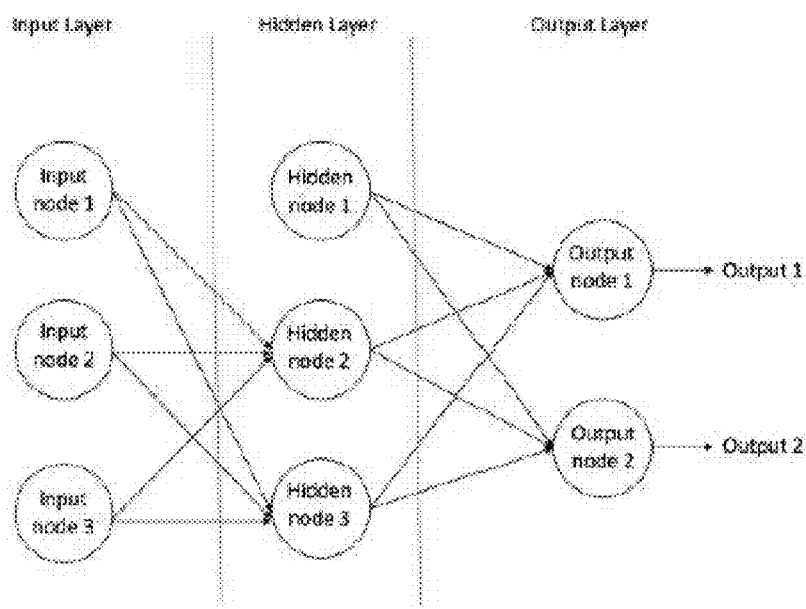

In some embodiments, a neural network is comprised of a series of layers termed "neurons." A typical neuron in a neural network is shown in FIG. 1A. As illustrated in FIG. 1B, in embodiments of neural networks, there is an input layer, to which data is presented; one or more internal, or "hidden," layers; and an output layer. A neuron may be connected to neurons in other layers via connections that have weights, which are parameters that control the strength of the connection. The number of neurons in each layer may be related to the complexity of the problem to be solved. The minimum number of neurons required in a layer may be determined by the problem complexity, and the maximum number may be limited by the ability of the neural network to generalize. The input neurons may receive data from data being presented and transmit that data to the first hidden layer through connections' weights, which are modified during training. The first hidden layer may process the data and transmit its result to the next layer through a second set of weighted connections. Each subsequent layer may "pool" the results from the previous layers into more complex relationships. In addition, whereas conventional software programs require writing specific instructions to perform a function, neural networks are programmed by training them with a known sample set and allowing them to modify themselves during (and after) training so as to provide a desired output such as an output value. After training, when a neural network is presented with new input data, it is configured to generalize what was "learned" during training and apply what was learned from training to the new previously unseen input data in order to generate an output associated with that input.

In some embodiments of a machine learning software module as described herein, a machine learning software module comprises a neural network such as a deep convolutional neural network. In some embodiments in which a convolutional neural network is used, the network is constructed with any number of convolutional layers, dilated layers or fully connected layers. In some embodiments, the number of convolutional layers is between 1-10 and the dilated layers between 0-10. In some embodiments, the number of convolutional layers is between 1-10 and the fully connected layers between 0-10.

Figure 2:
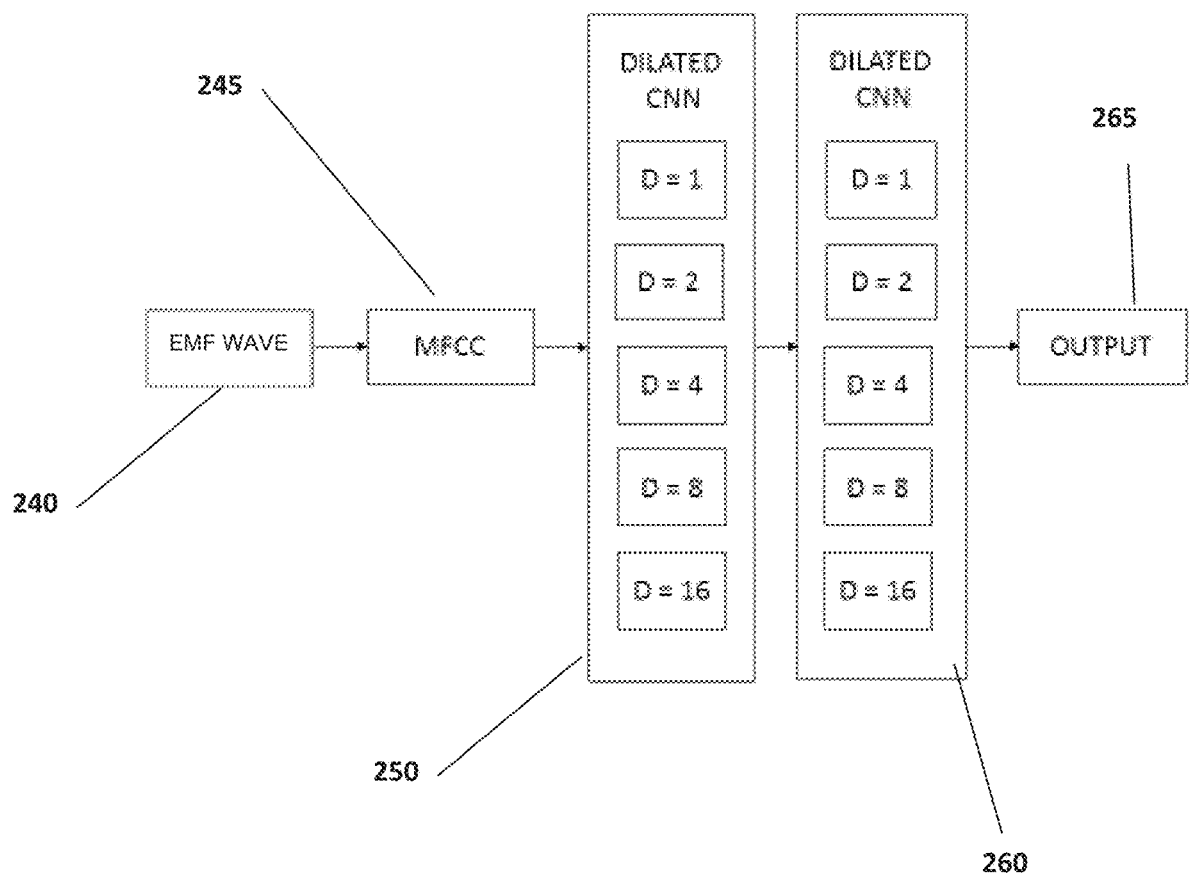
FIG. 2 shows a schematic representing an exemplary machine learning software module.

FIG. 2 shows a flow chart representing the architecture of an exemplary embodiment a machine learning software module. In this exemplary embodiment, raw EMF 240 of the individual is used to extract the MFCC features 245 which are fed into the deep learning module. The machine learning software module comprises two blocks of Dilated Convolutional neural networks 250, 260. Each block has 5 dilated convolution layers with dilation rates D=1, 2, 4, 8, 16. The number of blocks, and the number of layers in each block can increase or decrease, so it is not limited to the configuration portrayed in FIG. 2.

Training Phase

A machine learning software module as described herein is configured to undergo at least one training phase wherein the machine learning software module is trained to carry out one or more tasks including data extraction, data analysis, and output generation.

In some embodiments of the software application described herein, the software application comprises a training module that trains the machine learning software module. The training module is configured to provide training data to the machine learning software module, said training data comprising, for example, EMF measurements and the corresponding abnormality data. In additional embodiments, said training data is comprised of simulated EMF data with corresponding simulated abnormality data. In some embodiments of a machine learning software module described herein, a machine learning software module utilizes automatic statistical analysis of data in order to determine which features to extract and/or analyze from an EMF measurement. In some of these embodiments, the machine learning software module determines which features to extract and/or analyze from an EMF based on the training that the machine learning software module receives.

In some embodiments, a machine learning software module is trained using a data set and a target in a manner that might be described as supervised learning. In these embodiments, the data set is conventionally divided into a training set, a test set, and, in some cases, a validation set. A target is specified that contains the correct classification of each input value in the data set. For example, a set of EMF data from one or more individuals is repeatedly presented to the machine learning software module, and for each sample presented during training, the output generated by the machine learning software module is compared with the desired target. The difference between the target and the set of input samples is calculated, and the machine learning software module is modified to cause the output to more closely approximate the desired target value. In some embodiments, a back-propagation algorithm is utilized to cause the output to more closely approximate the desired target value. After a large number of training iterations, the machine learning software module output will closely match the desired target for each sample in the input training set. Subsequently, when new input data, not used during training, is presented to the machine learning software module, it may generate an output classification value indicating which of the categories the new sample is most likely to fall into. The machine learning software module is said to be able to "generalize" from its training to new, previously unseen input samples. This feature of a machine learning software module allows it to be used to classify almost any input data which has a mathematically formulatable relationship to the category to which it should be assigned.

In some embodiments of the machine learning software module described herein, the machine learning software module utilizes an individual learning model. An individual learning model is based on the machine learning software module having trained on data from a single individual and thus, a machine learning software module that utilizes an individual learning model is configured to be used on a single individual on whose data it trained.

In some embodiments of the machine training software module described herein, the machine training software module utilizes a global training model. A global training model is based on the machine training software module having trained on data from multiple individuals and thus, a machine training software module that utilizes a global training model is configured to be used on multiple patients/individuals.

In some embodiments of the machine training software module described herein, the machine training software module utilizes a simulated training model. A simulated training model is based on the machine training software module having trained on data from simulated EMF measurements. A machine training software module that utilizes a simulated training model is configured to be used on multiple patients/individuals.

In some embodiments, the use of training models changes as the availability of EMF data changes. For instance, a simulated training model may be used if there are insufficient quantities of appropriate patient data available for training the machine training software module to a desired accuracy. This may be particularly true in the early days of implementation, as few appropriate EMF measurements with associated abnormalities may be available initially. As additional data becomes available, the training model can change to a global or individual model. In some embodiments, a mixture of training models may be used to train the machine training software module. For example, a simulated and global training model may be used, utilizing a mixture of multiple patients' data and simulated data to meet training data requirements.

Unsupervised learning is used, in some embodiments, to train a machine training software module to use input data such as, for example, EMF data and output, for example, a diagnosis or abnormality. Unsupervised learning, in some embodiments, includes feature extraction which is performed by the machine learning software module on the input data. Extracted features may be used for visualization, for classification, for subsequent supervised training, and more generally for representing the input for subsequent storage or analysis. In some cases, each training case may consist of a plurality of EMF data.

Machine learning software modules that are commonly used for unsupervised training include k-means clustering, mixtures of multinomial distributions, affinity propagation, discrete factor analysis, hidden Markov models, Boltzmann machines, restricted Boltzmann machines, autoencoders, convolutional autoencoders, recurrent neural network autoencoders, and long short-term memory autoencoders. While there are many unsupervised learning models, they all have in common that, for training, they require a training set consisting of biological sequences, without associated labels.

A machine learning software module may include a training phase and a prediction phase. The training phase is typically provided with data in order to train the machine learning algorithm. Non-limiting examples of types of data inputted into a machine learning software module for the purposes of training include medical image data, clinical data (e.g. from a health record), encoded data, encoded features, or metrics derived from an electromagnetic field. Data that is inputted into the machine learning software module is used, in some embodiments, to construct a hypothesis function to determine the presence of an abnormality. In some embodiments, a machine learning software module is configured to determine if the outcome of the hypothesis function was achieved and based on that analysis make a determination with respect to the data upon which the hypothesis function was constructed. That is, the outcome tends to either reinforce the hypothesis function with respect to the data upon which the hypothesis functions was constructed or contradict the hypothesis function with respect to the data upon which the hypothesis function was constructed. In these embodiments, depending on how close the outcome tends to be to an outcome determined by the hypothesis function, the machine learning algorithm will either adopts, adjusts, or abandon the hypothesis function with respect to the data upon which the hypothesis function was constructed. As such, the machine learning algorithm described herein dynamically learns through the training phase what characteristics of an input (e.g. data) is most predictive in determining whether the features of a patient EMF display any abnormality.

For example, a machine learning software module is provided with data on which to train so that it, for example, is able to determine the most salient features of a received EMF data to operate on. The machine learning software modules described herein train as to how to analyze the EMF data, rather than analyzing the EMF data using pre-defined instructions. As such, the machine learning software modules described herein dynamically learn through training what characteristics of an input signal are most predictive in determining whether the features of an EMF display any abnormality.

In some embodiments, the machine learning software module is trained by repeatedly presenting the machine learning software module with EMF data along with, for example, abnormality data. The term "abnormality data" is meant to comprise data concerning the existence or non-existence of an abnormality in an organ or tissue. Any disease, disorder or condition associated with the abnormality is included in the abnormality data if available. For example, information concerning a subject displaying symptoms of hypertension, ischemia or shortness of breath is included as abnormality data. Information concerning a subject's lack of any irregular health condition is also included as abnormality data. In the case where EMF data is generated by computer simulation, the abnormality data may be used as additional data being used to simulate the organ or tissue. In some embodiments, more than one abnormality is included in the abnormality data. In additional embodiments, more than one condition, disease or disorder is included in the abnormality data.

In some embodiments, training begins when the machine learning software module is given EMF data and asked to determine the presence of an abnormality. The predicted abnormality is then compared to the true abnormality data that corresponds to the EMF data. An optimization technique such as gradient descent and backpropagation is used to update the weights in each layer of the machine learning software module so as to produce closer agreement between the abnormality probability predicted by the machine learning software module, and the presence of the abnormality. This process is repeated with new EMF data and abnormality data until the accuracy of the network has reached the desired level. In some embodiments the abnormality data additionally comprises the type and location of the abnormality. For example, the abnormality data may indicate that an abnormality is present, and that said abnormality is an ischemia of the left ventricle of the heart. In this case, training begins when the machine learning software module is given the corresponding EMF data and asked to determine the type and location of the abnormality. An optimization technique is used to update the weights in each layer of the machine learning software module so as to produce closer agreement between the abnormality data predicted by the machine learning software module, and the true abnormality data. This process is repeated with new EMF data and abnormality data until the accuracy of the network has reached the desired level. In some embodiments, the abnormality data additionally comprises a known resulting or related disease, disorder or condition associated with an identified abnormality. For example, the abnormality data may indicate that the subject possesses an atrial flutter and arterial coronary disease. In cases such as this, training begins when the machine learning software module is given the corresponding EMF data and asked to determine the presence of a condition, disorder or disease. The output data is then compared to the true abnormality data that corresponds to the EMF data. An optimization technique is used to update the weights in each layer of the machine learning software module so as to produce closer agreement between the abnormality probability predicted by the machine learning software module, and the actual abnormality. This process is repeated with new EMF data and abnormality data until the accuracy of the network has reached the desired level. Following training with the appropriate abnormality data given above, the machine learning module is able to analyze an EMF measurement and determine the presence of an abnormality, the type and location of said abnormality and the conditions associated with such.

In some embodiments of the machine learning software modules described herein, the machine learning software module receives EMF data and directly determines the abnormality probability of the subject, wherein the abnormality probability comprises the probability that the EMF measurement is associated with the abnormality of the subject.

In some embodiments, the machine learning software module is trained on a single continuous EMF measurement with corresponding abnormality data over a period of time. This can greatly increase the amount of training data available to train a machine learning software module. For example, in a EMF recording consisting of N continuous 10-second segments with accompanying abnormality data, one can generate at least N*N pairs of such segments to train on.

In some embodiments, an individual's abnormality data is inputted by the individual of the system. In some embodiments, an individual's abnormality data is inputted by an entity other than the individual. In some embodiments, the entity can be a healthcare provider, healthcare professional, family member or acquaintance. In additional embodiments, the entity can be the instantly described system, device or an additional system that analyzes EMF measurements and provides data pertaining to physiological abnormalities.

In some embodiments, a strategy for the collection of training data is provided to ensure that the EMF measurements represent a wide range of conditions so as to provide a broad training data set for the machine learning software module. For example, a prescribed number of measurements during a set period of time may be required as a section of a training data set. Additionally these measurements can be prescribed as having a set amount of time between measurements. In some embodiments, EMF measurements taken with variations in a subject's physical state may be included in the training data set. Examples of physical states include accelerated heart rate and enhanced brain signaling. Additional examples include the analysis of a subjects EMF data under the influence of medication or during the course of medical treatment.

In some embodiments, training data may be generated by extracting random overlapping segments of EMF measurements performed by the subject. In some embodiments, training examples can be provided by measurement recordings, models or algorithms that are independent of the subject. Any mixture or ratio of subject and non-subject training measurements can be used to train the system. For example, a network may be trained using 5 EMF segments extracted from a subject's measurements, and 15,000 EMF segments taken from another subject's recordings. Training data can be acquired using two different methods. The first method is to directly measure the EMF measurements over a subject's chest. The second method involves creating an accurate electro-anatomical model of the heart. This electro-anatomical model can be used to generate EMF measurements of both healthy and diseased subjects. The measurements are acquired by applying the Biot-Savart Law. This calculates the magnetic field vector at a given point in space, caused by a specific movement of current. After the EMF measurements have been acquired or calculated, they are fed into the network with a classification label, describing both the presence and location of diseased tissue.

In general, a machine learning algorithm is trained using a large patient database of medical image and/or clinical data and/or encoded data from one or more EMF measurements and/or any features or metrics computed from the above said data with the corresponding ground-truth values. The training phase constructs a transformation function for predicting probability of an abnormality in an unknown patient's organ or tissue by using the medical image and/or clinical data and/or encoded data from the one or more EMF measurements and/or any features or metrics computed from the above said data of the unknown patient. The machine learning algorithm dynamically learns through training what characteristics of an input signal are most predictive in determining whether the features of a patient EMF data display any abnormality. A prediction phase uses the constructed and optimized transformation function from the training phase to predict the probability of an abnormality in an unknown patient's organ or tissue by using the medical image and/or clinical data and/or encoded data from the one or more EMF measurements and/or any features or metrics computed from the above said data of the unknown patient.

Prediction Phase

Following training, the machine learning algorithm is used to determine, for example, the presence or absence of an abnormality on which the system was trained using the prediction phase. With appropriate training data, the system can identify the location and type of an abnormality, and present conditions associated with such abnormality. For example, an EMF measurement is taken of a subject's brain and appropriate data derived from the EMF measurement is submitted for analysis to a system using the described trained machine learning algorithm. In these embodiments, a machine learning software algorithm detects an abnormality associated with epilepsy. In some embodiments, the machine learning algorithm further localizes an anatomical region associated with an abnormality such as, for example, localizing an area of the brain of an individual associated with epilepsy in the individual based on an EMF measurement of individual.

An additional example, a subject is known to possess arterial ischemia and has EMF measurements recorded before and after treatment with a medication. The medical image and/or clinical data and/or encoded data from the EMF measurements and/or features and/or metrics derived from the said data are submitted for analysis to a system using the described trained machine learning algorithm in order to determine the effectiveness of the medication on abnormal blood flow using the prediction phase.

The prediction phase uses the constructed and optimized hypothesis function from the training phase to predict the probability of an abnormality in an unknown patient's organ or tissue by using the medical image and/or clinical data and/or encoded data from the EMF measurements and/or any features or metrics computed from the above said data of the unknown individual.

In some embodiments, in the prediction phase, the machine learning software module can be used to analyze data derived from its EMF measurement independent of any system or device described herein. In these instances, the new data recording may provide a longer signal window that required for determining the presence of a subject's abnormality. In some embodiments, the longer signal can be cut to an appropriate size, for example 10 seconds and then can be used in the prediction phase to predict the probability of an abnormality of the new patient data.

In some embodiments, a probability threshold can be used in conjunction with a final probability to determine whether or not a given recording matches the trained abnormality. In some embodiments, the probability threshold is used to tune the sensitivity of the trained network. For example, the probability threshold can be 1%, 2%, 5%, 10%, 15%, 20%, 25%, 30%, 35%, 40%, 45%, 50%, 55%, 60%, 65%, 70%, 75%, 80%, 85%, 90%, 95%, 98% or 99%. In some embodiments, the probability threshold is adjusted if the accuracy, sensitivity or specificity falls below a predefined adjustment threshold. In some embodiments, the adjustment threshold is used to determine the parameters of the training period. For example, if the accuracy of the probability threshold falls below the adjustment threshold, the system can extend the training period and/or require additional measurements and/or abnormality data. In some embodiments, additional measurements and/or abnormality data can be included into the training data. In some embodiments, additional measurements and/or abnormality data can be used to refine the training data set.

Input Data

As described herein, a machine learning software module is typically provided with data (input) in order to train the machine learning software module as to how to analyze an EMF to determine, for example, the presence of an abnormality. Input data is also used by a machine learning software module to generate an output.

An input to a machine learning algorithm as described herein, is in some embodiments, is data transmitted to the machine learning algorithm by a device or a system which includes an EMF sensor. In some embodiments of the devices, systems, software, and methods described herein, data that is received by a machine learning algorithm software module from an electromagnetic sensor as an input may comprise EMF data expressed in a standard unit of measurement such as, for example, Tesla.

In some embodiments, sensed EMF data comprises an overall or total EMF generated by a body of an individual based on numerous different currents generated by the body of the individual. That is, in some embodiments, one or more EMF sensors sense an EMF that comprises an EMF associated with entire individual and is not specific to a single organ or tissue. Likewise, in some embodiments, an EMF that is sensed from an individual that is associated with a portion of the individual but not specific to a single organ or tissue.

In some embodiments, sensed EMF data comprises an EMF that is in proximity to an individual or a portion of the body of the individual and comprises an EMF associated with a single organ, organ system, or tissue. For example, in some embodiments, one or more EMF sensors are positioned in proximity to a chest of an individual and sense an EMF associated with a heart of the individual. For example, in some embodiments, one or more EMF sensors are positioned in proximity to a head of an individual and sense an EMF associated with a brain of the individual. For example, in some embodiments, one or more EMF sensors are positioned in proximity to a chest of an individual and sense an EMF associated with a cardio-pulmonary system (i.e. the heart and lungs).

In some embodiments, a machine learning software module is configured to receive an encoded length of EMF data as an input and to determine the window length of the input data. For example, an input to a machine learning software module in some embodiments described herein is 100 seconds of encoded EMF data, and the machine learning software module selects a 10 second segment within the 100 second data sample for examination. In some embodiments, the input is segmented into multiple inputs, any number of which is analyzed independently. Any number of these analyses may be used to determine the final output.

In some embodiments, a device, system, or method as described herein is configured to sense and/or receive data comprising data associated with an individual. Data is sensed, in some embodiments, by an electromagnetic field sensor that is a component of a device, system, or method described herein. Data is received, in some embodiments, by transmission of data to a software algorithm as described herein by a source other than an EMF that is a component of a device, system, or method that also includes the software algorithm. That is, data, in some embodiments, is received from a source remote from the device, system, or method that includes the software algorithm. In some embodiments, data that is received comprises stored data. In some embodiments, data that is received comprises data that is generated by a software module. In general, sensed and/or received data comprises an input to a machine learning algorithm as described herein. An input is used to train a machine learning algorithm and/or is used by the machine learning algorithm to carry out an analysis or prediction.

Data as described herein comprises EMF data as well as other information associated with an individual. Non-limiting examples of data used as an input for a machine learning algorithm as described herein includes a medical record (e.g. an electronic health record), a diagnosis, a lab value, a vital sign, a prognosis, an electrocardiogram, a radiology image (including ultrasound, CT scan, MRI, and X-ray), an electroencephalogram, and a pathology report. In some embodiments, two or more different types of data are combined and/or correlated by the software algorithms described herein.

EMF data, in some embodiments, is used to generate other types of data that are used by the software algorithms described herein. For example, EMF data, in some embodiments, is used to generate medical image data which, in some embodiments, is achieved using Magnetic Field Maps (MFM). In some embodiments, EMF data is used to generate medical image data using Pseudo-Current Density (PCD) maps. In some embodiments, EMF data is used to generate medical data using Spatio-Temporal Activation Graphs (STAG).

EMF data, in some embodiments, is used to generate clinical data such as MCG, MEG and MGG measurements.

In some embodiments, input to a software algorithm as described herein comprises EMF data which is encoded into some other form of data and the features or metrics computed from the encoded data such as, for example, MFCC.

In some embodiments, input to a software algorithm as described herein is generated by a computer. For example, in some embodiments, an input to a software algorithm as described herein comprises data generated by computer simulation. In some embodiments, a computer simulation generates an image or other representation of an organ or other tissue (including skin, bone, and blood). In some embodiments, a computer simulation generates an image or representation of a flow of a fluid such as, for example, blood, lymph, or bile. In some embodiments, a computer simulation generates an image or representation of a flow of an electric current. Non-limiting examples of additional inputs generated by a computer simulation include a medical record (e.g. an electronic health record), a diagnosis, a lab value, a vital sign, a prognosis, an electrocardiogram, a radiology image (including ultrasound, CT scan, MRI, and X-ray), an electroencephalogram, and a pathology report.

Data Filtering

In some embodiments of the devices, systems, software, and methods described herein, data that is received by a machine learning algorithm software module from an electromagnetic sensor as an input may comprise EMF data that has been filtered and or modified. In some embodiments, filtering comprises a removal of noise or artifact from a sensed electromagnetic field data. Artifact or noise may comprise, for example, ambient electromagnetic signals that are sensed together with electromagnetic data sensed from an individual.

In some embodiments of the devices, systems, software, and methods described herein, sensed EMF data is filtered prior to and/or after transmission of said data to a processor. Filtering of sensed EMF data may, for example, comprise the removal of ambient signal noise from a sensed EMF data. Signal noise may, for example, comprises ambient EMF data generated by, for example, electronic devices, the earth's magnetosphere, electrical grids, or other individuals (i.e. not individuals whose EMF data is being targeted).

In some embodiments, sensed EMF data is converted to another form of data or signal which then undergoes a signal filtering process. In some embodiments, a device or system includes a processor including software that is configured to convert sensed EMF data to another form of data or signal. The process of converting sensed EMF data to another form of data or signal typically comprises an encoding process, wherein a first form of data is converted into a second form of data or signal.

In some embodiments, sensed EMF data is encoded into an audio signal which undergoes a filtering process. In some embodiments, sensed EMF data is encoded into an audio signal or alternatively, a signal having the morphology of an audio signal.

In some embodiments, sensed EMF data is encoded into an audio signal which is further processed into a Mel-Frequency Cepstrum from which one or more Mel-Frequency Cepstrum Coefficients ("MFCC") are derived. Mel-Frequency Cepstrum ("MFC") represents a short term power spectrum of a sound. It is based on a linear cosine transform of a log power spectrum on a nonlinear mel scale of frequency. Mel-frequency cepstral coefficients ("MFCCs") collectively make up an MFC. These are derived from a type of cepstral representation of the audio. In MFC, frequency bands are equally spaced on the mel-scale as compared to the linearly-spaced frequency bands used in the normal cepstrum. This equally spaced frequency bands allows for better representation of audio.

In some embodiments, a sensed EMF signal is filtered by converting the sensed EMF data into an audio signal or a signal having the morphology of an audio signal wave, and then generating MFCCs.

MFCCs help in identifying the components of the audio signal that are able to differentiate between important content and background noise.

In general, steps for filtering an audio signal derived from sensed EMF data comprise: In a first step, the audio signal is framed into short frames. In a second step, the periodogram estimate of the power spectrum for each frame is calculated. In a third step, a mel filterbank is applied to the power spectrum and sum the energy in each filter. In a fourth step, the logarithm of all the filterbank energies is determined and the DCT of the log filterbank energies is calculated. In a fifth step, only the first 20 DCT coefficients are kept, and the rest are discarded.

Once filtered, the filtered data is transmitted to a machine learning algorithm for analysis. The algorithm described herein is capable of classifying and characterizing the physiological health of human body tissues. The algorithm is designed to analyze input data and determine the presence and location of diseased tissue in the organ(s) recorded by aforementioned sensors.

Devices and Systems

In some embodiments EMF data is sensed using a device or system. In some embodiments, a device or system comprises one or more EMF sensors. In some of these embodiments, the device or system is configured to include a machine learning software module as described herein. In some of these embodiments, the device or system is configured to transmit a sensed EMF to a machine learning software module not included as part of the device or system. EMF data that is sensed using an electromagnetic sensor comprises electromagnetic data associated with a passage of a current through a cell, tissue, and/or organ of an individual, such as, for example, the heart of the individual. Generally, described herein are devices and systems that comprise digital processing devices.

In some embodiments of devices and systems described herein, a device and/or a system comprises a digital processing device configured to run a software application as described herein. In further embodiments, a digital processing device includes one or more hardware central processing units (CPUs) or general purpose graphics processing units (GPGPUs) that carry out the device's functions. In still further embodiments, the digital processing device further comprises an operating system configured to perform executable instructions. In some embodiments, the digital processing device is optionally connected to a computer network. In further embodiments, the digital processing device is optionally connected to the Internet such that it accesses the World Wide Web. In still further embodiments, the digital processing device is optionally connected to a cloud computing infrastructure. In other embodiments, the digital processing device is optionally connected to an intranet. In other embodiments, the digital processing device is optionally connected to a data storage device.

In accordance with the description herein, suitable digital processing devices include, by way of non-limiting examples, server computers, desktop computers, laptop computers, notebook computers, sub-notebook computers, netbook computers, netpad computers, handheld computers, and tablet computers.

In some embodiments, the digital processing device includes an operating system configured to perform executable instructions. The operating system is, for example, software, including programs and data, which manages the device's hardware and provides services for execution of applications. Non-limiting examples of suitable operating systems include FreeBSD, OpenBSD, NetBSD®, Linux, Apple® Mac OS X Server®, Oracle® Solaris®, Windows Server®, and Novell® NetWare®. Those of skill in the art will recognize that suitable personal computer operating systems include, by way of non-limiting examples, Microsoft® Windows®, Apple® Mac OS X®, UNIX®, and UNIX-like operating systems such as GNU/Linux®. In some embodiments, the operating system is provided by cloud computing.

In some embodiments, a digital processing device includes a storage and/or memory device. The storage and/or memory device is one or more physical apparatuses used to store data or programs on a temporary or permanent basis. In some embodiments, the device is volatile memory and requires power to maintain stored information. In some embodiments, the device is non-volatile memory and retains stored information when the digital processing device is not powered. In further embodiments, the non-volatile memory comprises flash memory. In some embodiments, the non-volatile memory comprises dynamic random-access memory (DRAM). In some embodiments, the non-volatile memory comprises ferroelectric random access memory (FRAM). In some embodiments, the non-volatile memory comprises phase-change random access memory (PRAM). In other embodiments, the device is a storage device including, by way of non-limiting examples, CD-ROMs, DVDs, flash memory devices, magnetic disk drives, magnetic tapes, optical disk drives, and cloud computing based storage. In further embodiments, the storage and/or memory device is a combination of devices such as those disclosed herein.

In some embodiments, the digital processing device includes a display to send visual information to a subject. In some embodiments, the digital processing device includes an input device to receive information from a subject. In some embodiments, the input device is a keyboard. In some embodiments, the input device is a pointing device including, by way of non-limiting examples, a mouse, trackball, track pad, joystick, game controller, or stylus. In some embodiments, the input device is a touch screen or a multi-touch screen. In other embodiments, the input device is a microphone to capture voice or other sound input. In other embodiments, the input device is a video camera or other sensor to capture motion or visual input. In still further embodiments, the input device is a combination of devices such as those disclosed herein.

Figure 3:
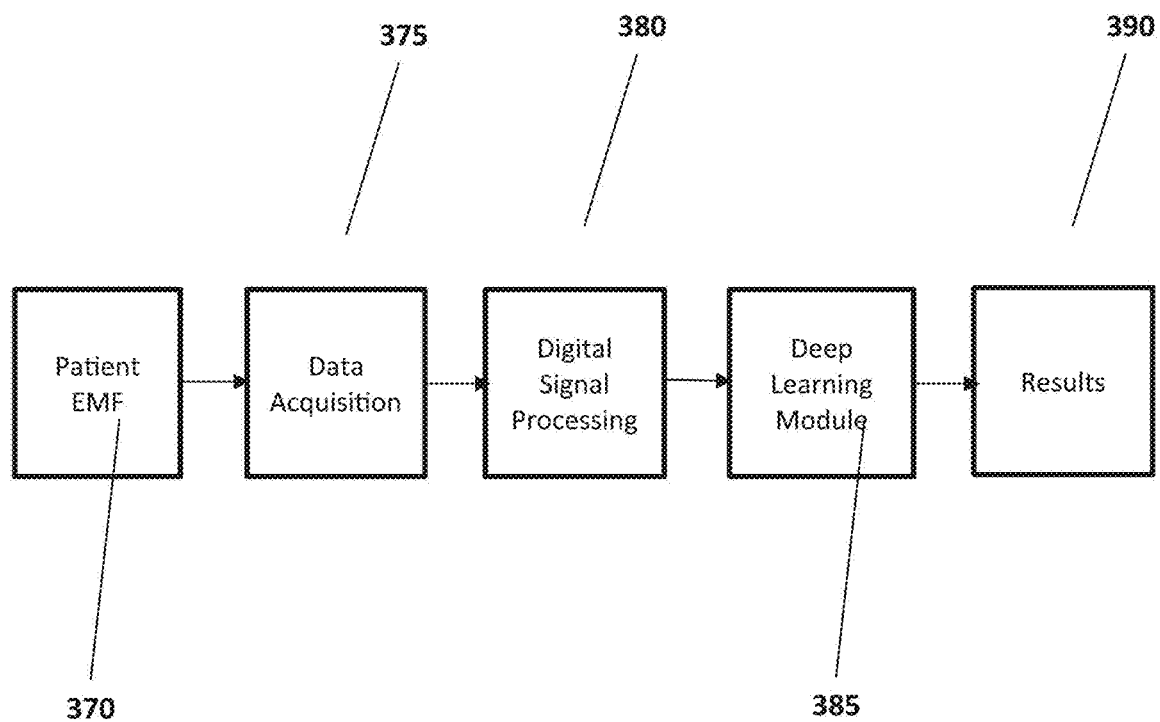
FIG. 3 shows a schematic representation of an exemplary device for sensing an analyzing an EMF.

FIG. 3 shows a schematic representation of an exemplary device for sensing an analyzing an EMF. The patient's organ emits an EMF 370 which is then acquired from the EMF sensing device 375. The data is then processed, filtered and analyzed by a Digital Signal Processing module 380 thereby removing noise if any and extracting important information from the data. The processed data is then fed into the deep learning module 385 consisting of dilated convolutional neural networks. The deep learning module detects ischemia and localizes to a particular region in an organ 490.

In various embodiments, the platforms, systems, media, and methods described herein include a cloud computing environment. In some embodiments, a cloud computing environment comprises a plurality of computing processors.

Figure 4:
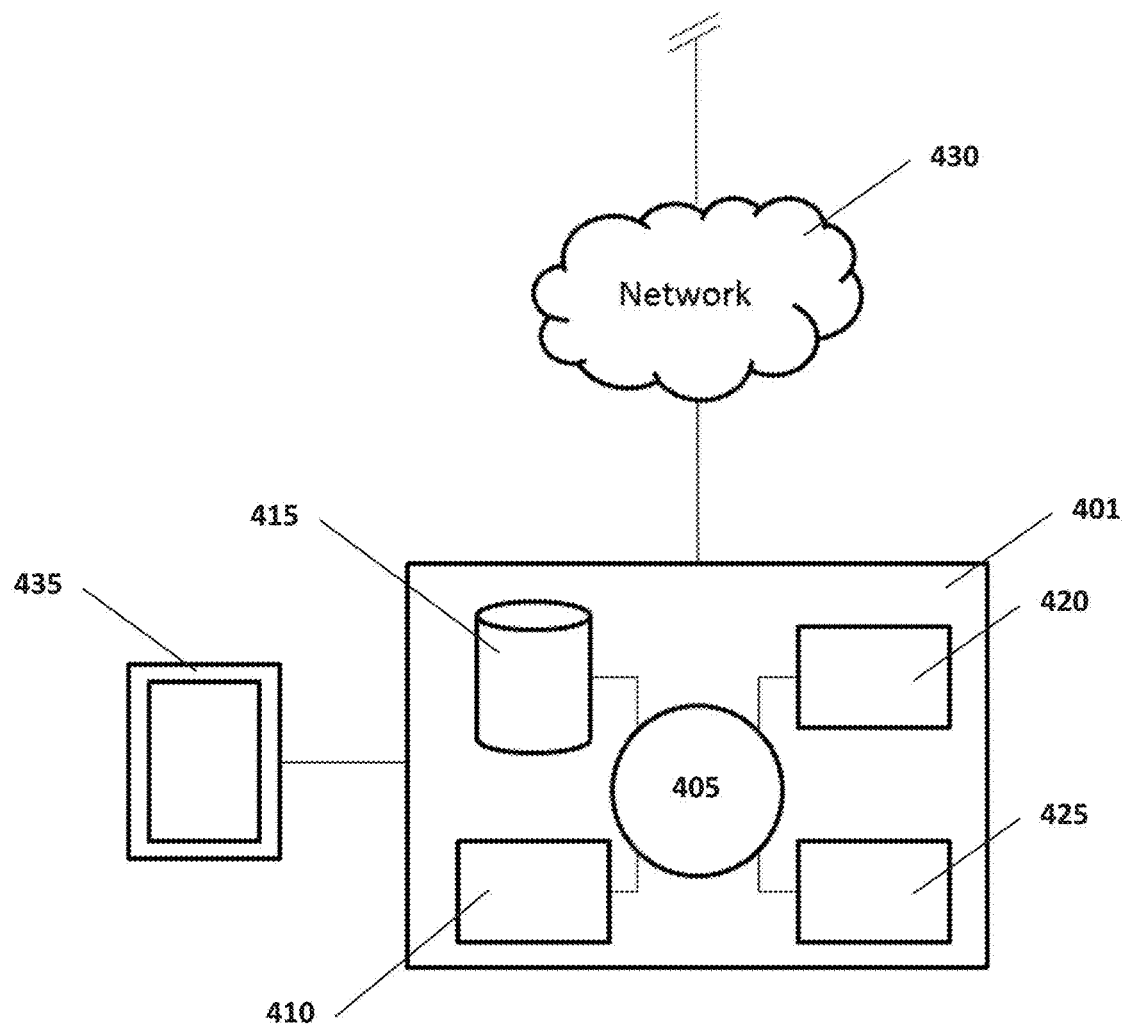
FIG. 4 shows a schematic of an exemplary embodiment of a system comprising a digital processing device.

FIG. 4 shows an exemplary embodiment of a system as described herein comprising a digital processing device 401. The digital processing device 401 includes a software application configured to perform data analysis such as analyzing an electromagnetic field to determine a condition of a subject. The device 401 is configured to run the software application that comprises a machine learning software module including training of the machine learning software module as described herein. In this embodiment, the digital processing device 401 includes a central processing unit (CPU, also "processor" and "computer processor" herein) 405, which can be a single core or multi-core processor, or a plurality of processors for parallel processing. The digital processing device 401 also includes either memory or a memory location 410 (e.g., random-access memory, read-only memory, flash memory), electronic storage unit 415 (e.g., hard disk), communication interface 420 (e.g., network adapter) for communicating with one or more other systems, and peripheral devices 425, such as cache. The memory 410, storage unit 415, interface 420 and peripheral devices 425 are configured to communicate with the CPU 405 through a communication bus (solid lines), such as a motherboard. The digital processing device 401 is, in some embodiments, operatively coupled to a computer network ("network") 430 with the aid of the communication interface 420. The network 430, in some embodiments, comprises the Internet. The network 430 in some embodiments is a telecommunication and/or data network.

The CPU 405 is configured to execute machine-readable instructions embodied in a software application or module. The instructions may be stored in a memory location, such as the memory 410.

The storage unit 415 in some embodiments is configured to store files, such as subject data, e.g., subject preferences, subject programs, and subject EMF data.

Methods as described herein can be implemented by way of machine (e.g., computer processor) executable code stored on an electronic storage location of the digital processing device 401, such as, for example, on the memory 410 or electronic storage unit 415. The machine executable or machine readable code can be provided in the form of a software application or software module. During use, the code can be executed by the processor 405. In some cases, the code can be retrieved from the storage unit 415 and stored on the memory 410 for ready access by the processor 405. In some situations, the electronic storage unit 415 can be precluded, and machine-executable instructions are stored on memory 410.

A remote device 435 is configured to communicate with the digital processing device 401, and may comprises any mobile computing device, non-limiting examples of which include a tablet computer, laptop computer, smartphone, or smartwatch. In some embodiments, a remote device 435 may comprises an integrated sensor or alternatively be coupled to a sensor that is configured to sense EMF data.

In some embodiments of the devices, systems, software, and methods described herein, sensed EMF data is transmitted directly from an electromagnetic sensor to a processor on a computing device that is encoded with a machine learning algorithm configured to analyze the received EMF data.

Described herein are software modules for sensing, analyzing, and optionally filtering data. Software comprising one or more software modules as described herein may, for example, be a component of a device or system that includes one or more sensors comprising an EMF sensor. This sensor records the magnetic fields that are naturally emitted by certain organs during physiological activity. Such organs may include the brain, heart or liver. In some embodiments, this sensor may take the form of a magnetometer, fluxgate, or superconducting quantum interference device (SQUID) fitted to perform biomagnetic measurements on an organ of interest.

In some embodiments of the devices and systems described herein, a device comprises a sensor, such as an optically pumped magnetometer (OPM) as a measurement tool, which, in some embodiments, utilizes nonradioactive self-contained alkali metal cells coupled with a closed pumping laser and photodetector setup to measure minute magnetic fields. In some embodiments of the devices and systems described herein, the devices and systems utilize OPMs in an n×n array (or grid) or alternative geometric configuration to collect magnetic field data at n discrete locations over, for example, a portion of a body of an individual such as a chest area, which, in some embodiments, is digitized using pickup electronics.

OPMs are typically configured to utilize nonradioactive self-contained alkali metal cells coupled with a closed pumping laser and photodetector setup to measure minute magnetic fields. Compared to superconducting quantum interference devices (SQUIDs), which are typically also used to detect these biomagnetic fields, OPM sensors are significantly smaller and typically do not require the use of cryogenic cooling.

The Earth's magnetic field is naturally present everywhere on Earth, and the amplitude is about 50 microtesla. OPM performance is enhanced in at least two exemplary ways in the presence of the Earth's ambient magnetic field. In a first OPM enhancing technique, a reference value representing Earth's magnetic field is used as part of a vector subtraction to isolate a signal of interest in an OPM. Another technique involves the use of a gradiometer for active noise cancellation for the OPM.

A sensor array configuration, as utilized in some embodiments of the devices and systems described herein, comprises a custom array configuration. In some embodiments, a sensor array configuration is customized to an individual's anatomy. In some embodiments, a sensor array configuration is customized to a location on the individual which is measured, such as a chest location or a head location. In some embodiments, a sensor array configuration is customized to a measurement type that a device is programmed to acquire. In some embodiments, a sensor array configuration is customized to be operatively coupled with a shield and/or an arm. In some embodiments, a sensor array configuration is interchangeable with a different array configuration—a user may perform with interchange. An array configuration, in some embodiments, comprises an arc (such as a generally curved shape) having a depth and comprising a radius from about 20 cm to about 50 cm or from about 10 cm to about 60 cm. An array configuration, such as an arc configuration, in some embodiments, comprises one or more variable inter-magnetometer distances and variable sensor densities. An array configuration, in some embodiments, comprises a concave structure (such as a concave structure configured to wrap or form around a body region, such as a head or chest). One or more magnetometers is positioned on at least a portion of a surface of the concave structure. A concave array configuration, in some embodiments, comprises one or more variable inter-magnetometer distances and variable sensor density.

In some embodiments, a sensor array n×n sensors. In some embodiments, a sensor array is a 2D rectangular array, such as a 2×2 array or a 4×4 array. In some embodiments, a sensor array is a 2D non-rectangular array, such as a 2×1 array or a 4×1 array. In some embodiments, a sensor array is a circular array or a semicircular array, such as a 3D array of sensors positioned in an arc or concave structure. In some embodiments, a sensor array is a 2D array or a 3D array. In some embodiments, a sensor of a sensor array comprises x, y, and z coordinates. An array, in some embodiments, comprises a single sensor, such as n×n=1×1. An array, in some embodiments, comprises two sensors, such as n×n=2×1. An array, in some embodiments, comprises three sensors. An array, in some embodiments, comprises four sensors. An array, in some embodiments, comprises nine sensors. An array, in some embodiments, comprises sixteen sensors. An array, in some embodiments, comprises 25 sensors. An array, in some embodiments, comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 sensors or more. In some embodiments, a sensor array comprises 8 sensors. In some embodiments, a sensor array comprises 16 sensors. In some embodiments, a sensor array comprises a single sensor housed in a single housing. In some embodiments, a sensor array comprises a plurality of sensors housed in a single housing, such as a housing having multiple sensor configurations or changeable sensor configurations. In some embodiments, a sensor array comprises a plurality of sensors housed in a plurality of housings. In some embodiments, a sensor array comprises a plurality of sensors, each sensor housed in a separate housing. In some embodiments, a first sensor and second sensor of a sensor array is different. In some embodiments, a first sensor and a second sensor of a sensor array is the same. In some embodiments, each sensor of a sensor array is unique. In some embodiments, each sensor of a sensor array is identical. In some embodiments, a subset of sensors within a sensor array is unique. In some embodiments, a subset of sensors within a sensor array is identical. Spatial positioning of a sensor in a sensor array is adjustable, such as by a user or automated by a controller. In some embodiments, spatial positioning of a sensor in a sensor array is fixed. In some embodiments, a number of sensors in a sensor array is selected based on an application. In some embodiments, a number of sensors in a sensor array is selected based on a type of measurement or a location of a measurement. An array, in some embodiments, comprises a single channel array or a multi-channel array. In some embodiments, increasing a number of sensors of a sensor array increases a resolution of a measurement taken by the array. In some embodiments, a sensor array of sensors is densely packed, such as substantially adjacent or proximal one another. An array of sensors is sparsely spaced, such as having a spacing between one another. In some embodiments, a subset of sensors of a sensor array is densely packed. In some embodiments, a subset of sensors of a sensor array is sparsely spaced or densely spaced. In some embodiments, centerpoints of any two sensors of a densely packed subset of sensors is spaced less than about: 5, 4.5, 4, 3.5, 3, 2.5, 2, 1.5, 1, 0.5, 0.1 centimeters (cm) apart. In some embodiments, centerpoints of densely packed sensors is spaced centerpoint to centerpoint from about 0.1 cm to about 2.0 cm or from about 0.1 cm to about 1.5 cm or from about 1.0 cm to about 2.0 cm. In some embodiments, centerpoints of any two sensors of a sparsely packed subset of sensors is spaced more than about: 1.5, 2, 2.5, 3, 3.5, 4, 4.5, 5, 8, 10 cm apart. In some embodiments, centerpoints of sparsely packed sensors is spaced centerpoint to centerpoint from about 1.5 cm to about 3 cm or from about 2 cm to about 5 cm or from about 2.5 cm to about 8 cm. In some embodiments, a center point is a central location of a sensor, such as a central axis. In some embodiments, a centerpoint of a circular sensor is a central point at which all other edge points are of equal distance.

In some embodiments, a densely packed array indicates intermagnetometer placement of less than 1.5 cm, while magnetometer placement of greater than about 1.5 cm constitutes a sparsely packed array.

In some embodiments, a housing is configured to house a sensor or a sensor array of sensors. In some embodiments, the housing is configured to accommodate a single configuration of sensor spacing within the housing. In some embodiments, the housing is configured to accommodate multiple configurations of sensor spacing within the housing. In some embodiments, the housing accommodates (i) adjusting sensor spacing, such as a dense spacing or a sparse spacing, or (ii) varying a number of sensors within the array. In some embodiments, a housing is a universal housing for a plurality of arrays and array configurations.

In some embodiments, a sensor is configured to sense a presence of or measure a parameter of a magnetic field. A sensor, in some embodiments, comprises a sensitivity to a magnetic field of about 10 femtotesla per root Hertz (fT/√Hz). A sensor, in some embodiments, comprises a sensitivity of from about 1 fT/√Hz to about 20 fT/√Hz. A sensor, in some embodiments, comprises a sensitivity of from about 5 fT/√Hz to about 15 fT/√Hz. A sensor, in some embodiments, comprises a sensitivity of from about 0.1 fT/√Hz to about 30 fT/√Hz. A sensor, in some embodiments, comprises a sensitivity of from about 0.5 fT/√Hz to about 12 fT/√Hz. A sensor, in some embodiments, comprises a sensitivity of from about 1 fT/√Hz to about 15 fT/√Hz. A sensor, in some embodiments, comprises a sensitivity of about: 0.001, 0.005, 0.01, 0.05, 0.1, 0.5, 1, 2, 3, 4, 5, 6, 7, 8, 10, 11, 12, 13, 14, 15, 16, 17, 18, 19, 20 fT/√Hz.

In some embodiments, a sensor does not require a cooling element, such as cryogenic cooling, to collect a measurement. In some embodiments, a sensor collects a measurement over a temperature range of from about 30 degrees Fahrenheit (F) to about 110 degrees F. In some embodiments, a sensor collects a measurement over a temperature range of from about 50 degrees F. to about 110 degrees F. In some embodiments, a sensor collects a measurement over a time period of from about 1 second to about 5 hours without a need for a cooling element. In some embodiments, a sensor collects a measurement over a time period of from about 1 second to about 1 hour without a need for a cooling element. In some embodiments, a sensor collect a measurement over a time period of from about 1 second to about 30 minutes without a need for a cooling element.

A noise source, in some embodiments, comprises a magnetic field strength. In some embodiments, a strength of a magnetic field of a noise source is measured in units of Tesla (T). Noise, such as ambient noise, in some embodiments, comprises a magnetic field strength of less than about 100 nanotesla (nT). Noise, in some embodiments, comprises a magnetic field strength of less than about 1000 nT. Noise, in some embodiments, comprises a magnetic field strength of less than about 500 nT. Noise, in some embodiments, comprises a magnetic field strength of less that about 200 nT. Noise, in some embodiments, comprises a magnetic field strength of less than about 120 nT. Noise, in some embodiments, comprises a magnetic field strength of less than about 80 nT. A noise source, such as a magnetic field of the Earth, in some embodiments, comprises a magnetic field strength of about 50 microtesla (mT). Noise, in some embodiments, comprises a magnetic field strength of from about 40 mT to about 60 mT. Noise, in some embodiments, comprises a magnetic field strength of from about 10 mT to about 100 mT. Noise, in some embodiments, comprises an amplitude component, a frequency component, or a combination thereof, and, in some embodiments, comprises both sources that is direct current (DC), alternating current (AC), or a combination of the two.

Methods

It should be understood, that any device, system, and/or software described herein is configured for use in or is captured by one or more steps of a method.

Examples

Cardiac Analysis

Figure 5A:
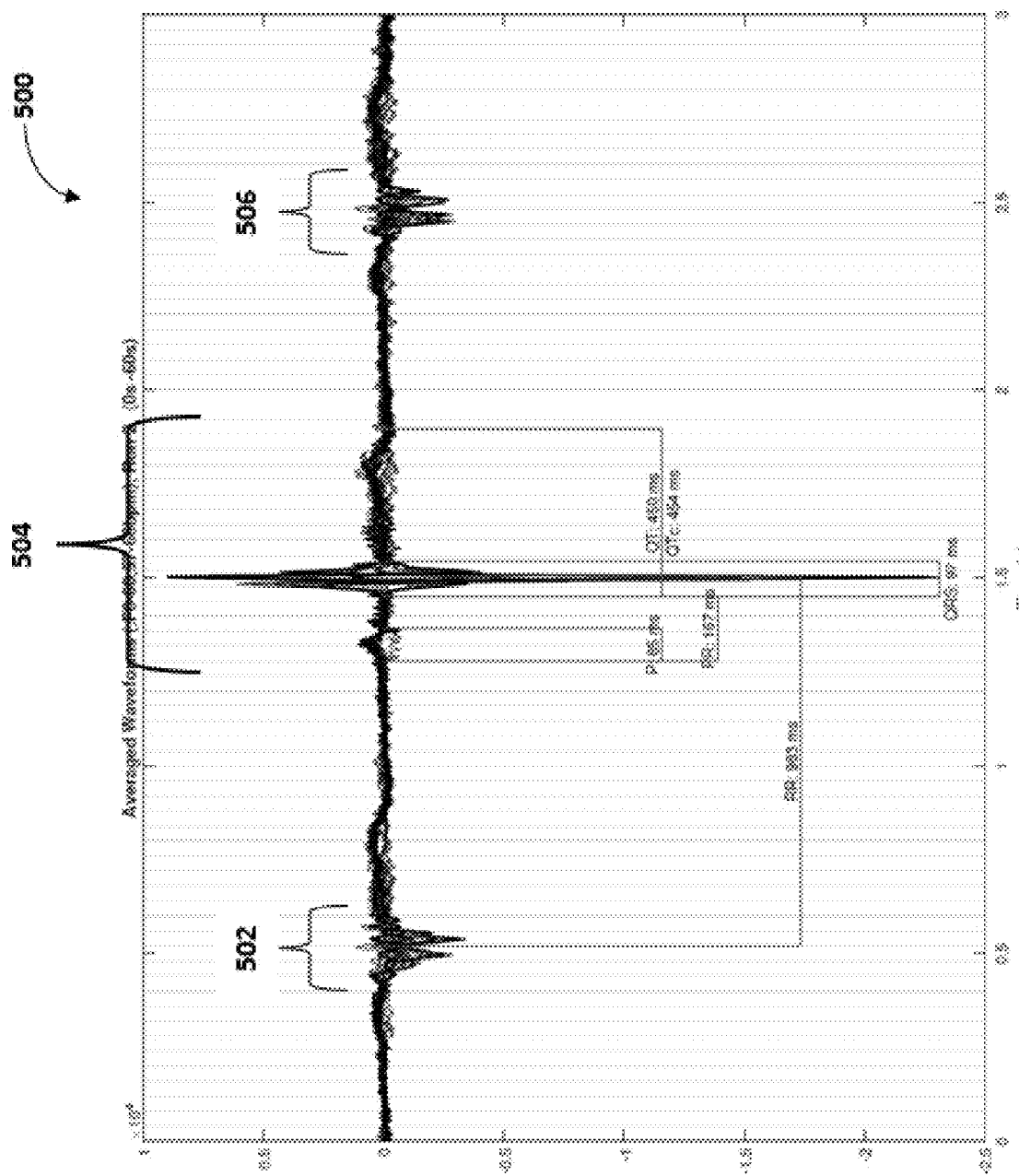
FIGS. 5A and 5B show examples of EMF data sensed from a plurality of OPM sensors positioned within proximity to a chest of an individual.

FIG. 5A shows an example of EMF data sensed from a plurality of OPM sensors positioned within proximity to a chest of an individual and, therefore, within proximity to a heart of the individual. The EMF sensed is associated with an electric current generated by cells of the heart of the individual. In this specific example, the EMF data that is sensed is from a 58 year old male using a plurality of OPM sensors positioned in proximity to the chest of the individual. The waveform 500 comprises EMF data in EM units (shown on the Y-axis), said data being sensed over time in seconds (shown on the X-axis).

More specifically, waveform 500 comprises a plurality of waveforms sensed from a plurality of OPM sensors positioned in proximity to the chest of the individual. In the example of FIG. 5A, the plurality of waveforms are positioned at different locations relative to the chest of the individual. In this example, the one or more OPM sensors are positioned in a sensor array where the array is itself positioned in proximity to the chest of the individual so that each of the plurality of OPM sensors is in a different position relative to the chest of the individual (although it should be understood that one or more OPM sensors may be arranged in other configurations in other embodiments of the systems, methods, devices, and software described herein and need not always be arranged in an array). In this example, waveform 500 comprises three separate individual waveforms 502, 504, and, 506. Waveforms 502, 504, and, 506 each correspond to a single PQRST complex as would be seen on a standard ECG. Therefore, each of the waveforms 502, 504, and, 506 correspond to an individual polarization and depolarization cardiac cycle or one heartbeat.

Figure 5B:
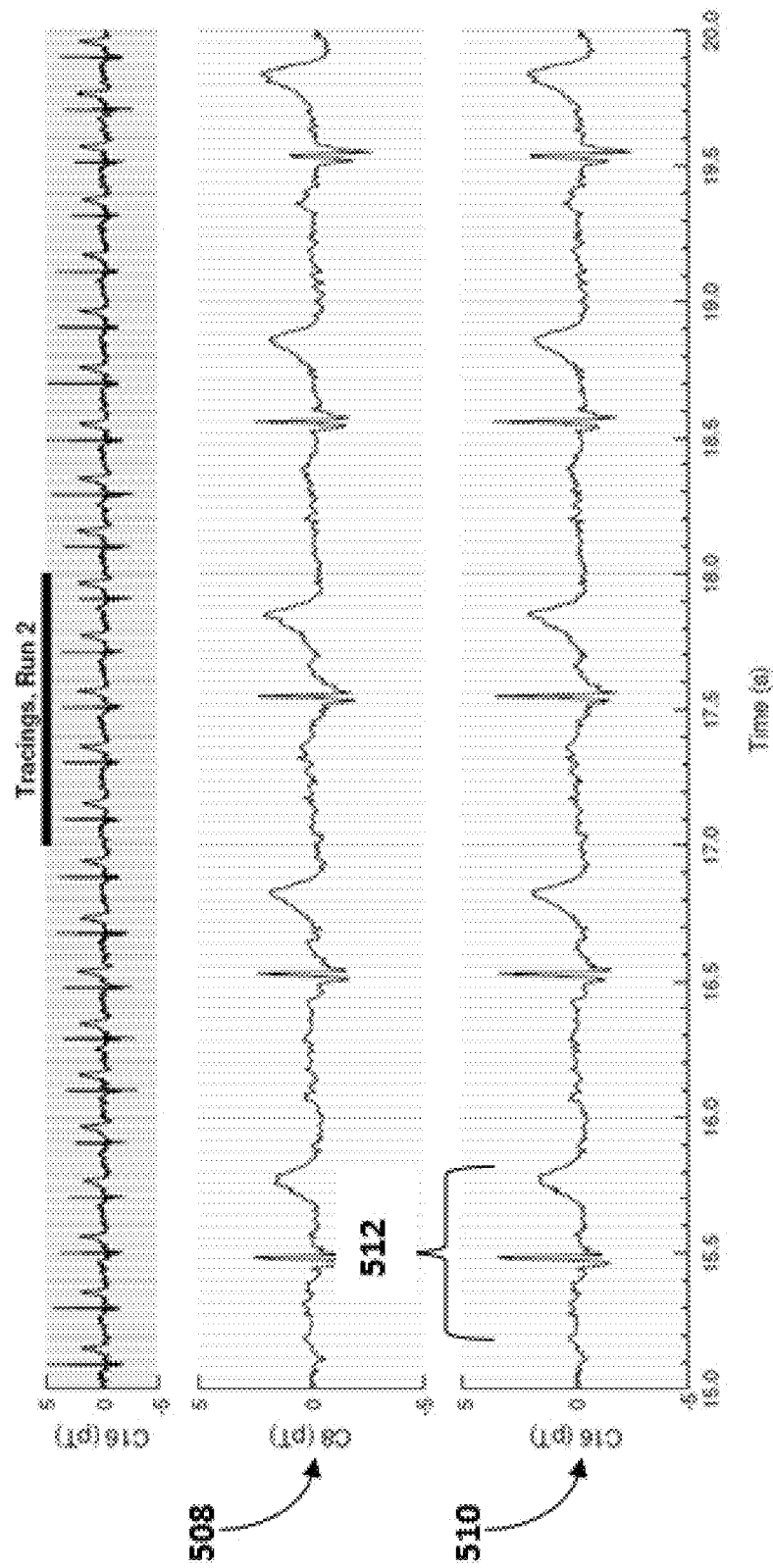

FIG. 5B shows examples of a plurality of single EMF waveforms (as compared to the single waveform of FIG. 5A which comprises a plurality of individual waveforms). In the examples of FIG. 5B, waveforms or tracings 508 and 510 each represent respective EMF signals sensed over the same period of time. In these examples, EMF data is sensed from the same 58 year old male using a plurality of OPM sensors as in the example of FIG. 5A. In the examples of FIG. 5B, tracings 508 and 510 are each a tracing representing a single waveform sensed over the same period of time and are different at least in part in that each of tracings 508 and 510 correspond to an EMF signal respectively sensed from a different OPM located at a different position relative to the chest (and therefore the heart) of the individual. That is, tracing 508 corresponds to a first EMF signal sensed from a first OPM sensor and tracing 510 corresponds to a second EMF signal sensed from a second OPM sensor where each of the first and second OPM sensors are located at different positions relative to the heart of the individual.

In a traditional ECG tracing, ten electrodes positioned at different locations on a body of an individual produce 12 ECG tracings, each corresponding to a different "view" of the heart. A particular ECG lead corresponds to a particular "view" of the heart in that each ECG tracing corresponds to a different spatial relationship between one or more ECG electrodes and the heart of the individual.

Similar to a traditional ECG tracing, each of tracings 508 and 510 represent a different "view" of the heart based on the position of the one or more EMF sensors relative to the chest of the individual. That is, current traveling through the heart of an individual generates a different EMF at different locations and as such is results in different appearing tracings based on the location of a sensor sensing that EMF. The tracings 508 and 510 each comprise a PQRST complex 512 (or, as shown, a plurality of PQRST complexes).

The exemplary data from FIGS. 5A and 5B are provided as input to a machine learning software module described herein. The machine learning software module receives the input and interrelates the data in numerous ways so that input data relating to the individual (including data related to the individual received concurrently to the input as well as data related to the individual received before and subsequent to receiving the input) is associated with the sensed EMF data shown in the examples of FIGS. 5A and 5B.

A machine learning software module as described herein correlates the age (58 years old in these examples) and gender (male in these examples) of the individual with one or more of the tracings 500, 508 and 510. Additional data relating to the individual may be provided that the machine learning software module may decide to correlate with the input as well. Non-limiting examples of the additional data comprises health records for the individual, including diagnoses, medications, lab results other EMF sensed data from the individual.

A machine learning software module as described herein further determines how to interrelate data from this individual and how to interrelate data of other individuals so as to generate a hypothesis function which is used to identify the presence of an abnormality in the individual and/or predict the occurrence of an abnormality in the individual.

Figure 6A:
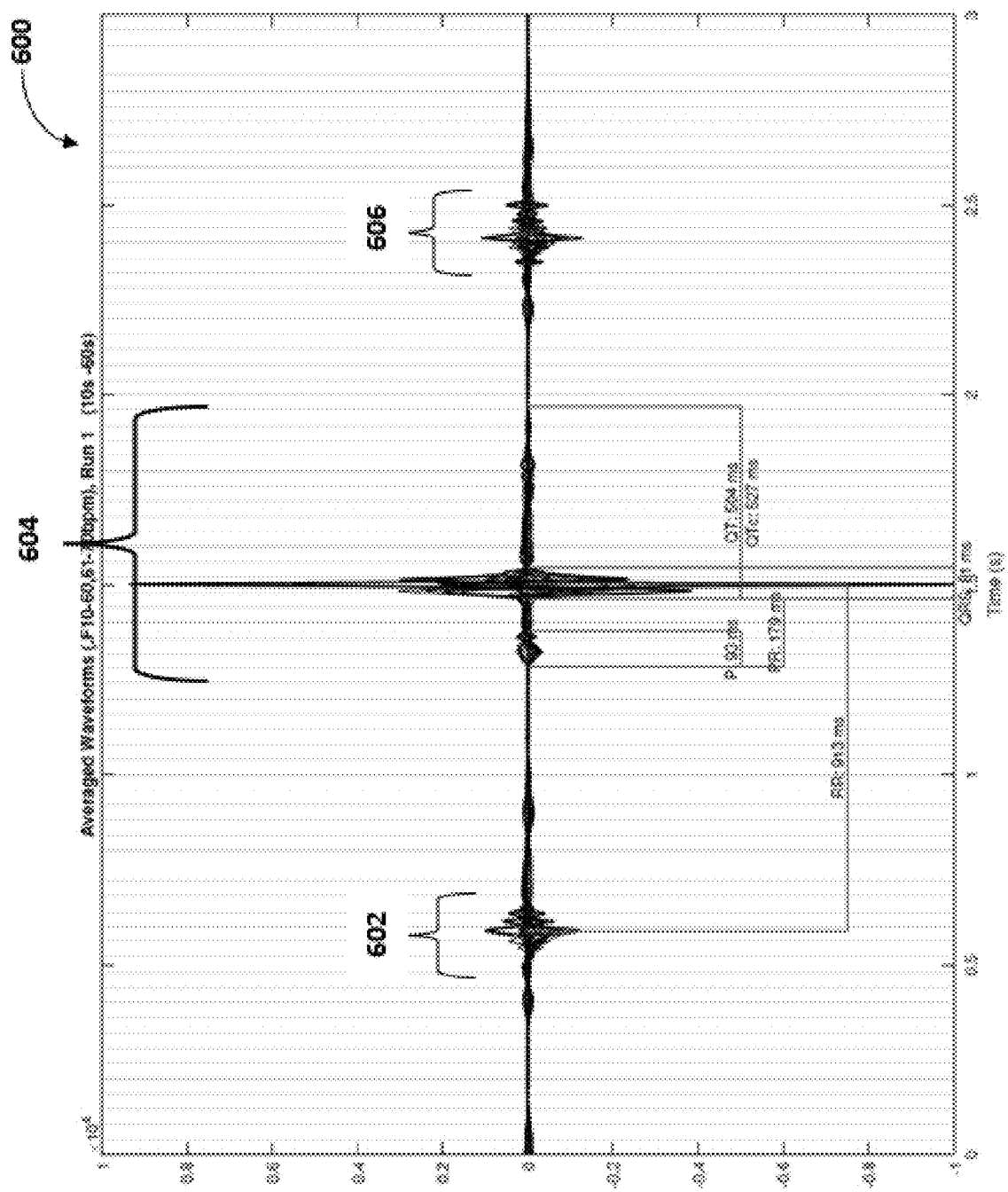
FIGS. 6A and 6B show examples of EMF data sensed from a plurality of SQUID sensors positioned within proximity to a chest of an individual.

FIG. 6A shows an example of EMF data sensed from a plurality of SQUID sensors positioned within proximity to a chest of an individual and, therefore, within proximity to a heart of the individual. The EMF sensed is associated with an electric current generated by cells of the heart of the individual. In this specific example, the EMF data that is sensed is from a 58 year old male using a plurality of SQUID sensors positioned in proximity to the chest of the individual. The waveform 600 comprises EMF data in EM units (shown on the Y-axis), said data being sensed over time in seconds (shown on the X-axis).

More specifically, waveform 600 comprises a plurality of waveforms sensed from a plurality of SQUID sensors positioned in proximity to the chest of the individual. In the example of FIG. 6A, the plurality of waveforms are positioned at different locations relative to the chest of the individual. In this example, the one or more SQUID sensors are positioned in a sensor array where the array is itself positioned in proximity to the chest of the individual so that each of the plurality of SQUID sensors is in a different position relative to the chest of the individual (although it should be understood that one or more SQUID sensors may be arranged in other configurations in other embodiments of the systems, methods, devices, and software described herein and need not always be arranged in an array). In this example, waveform 600 comprises three separate individual waveforms 602, 604, and, 606. Waveforms 602, 604, and, 606 each correspond to a single PQRST complex as would be seen on a standard ECG. Therefore, each of the waveforms 602, 604, and, 606 correspond to an individual polarization and depolarization cardiac cycle or one heartbeat.

Figure 6B:
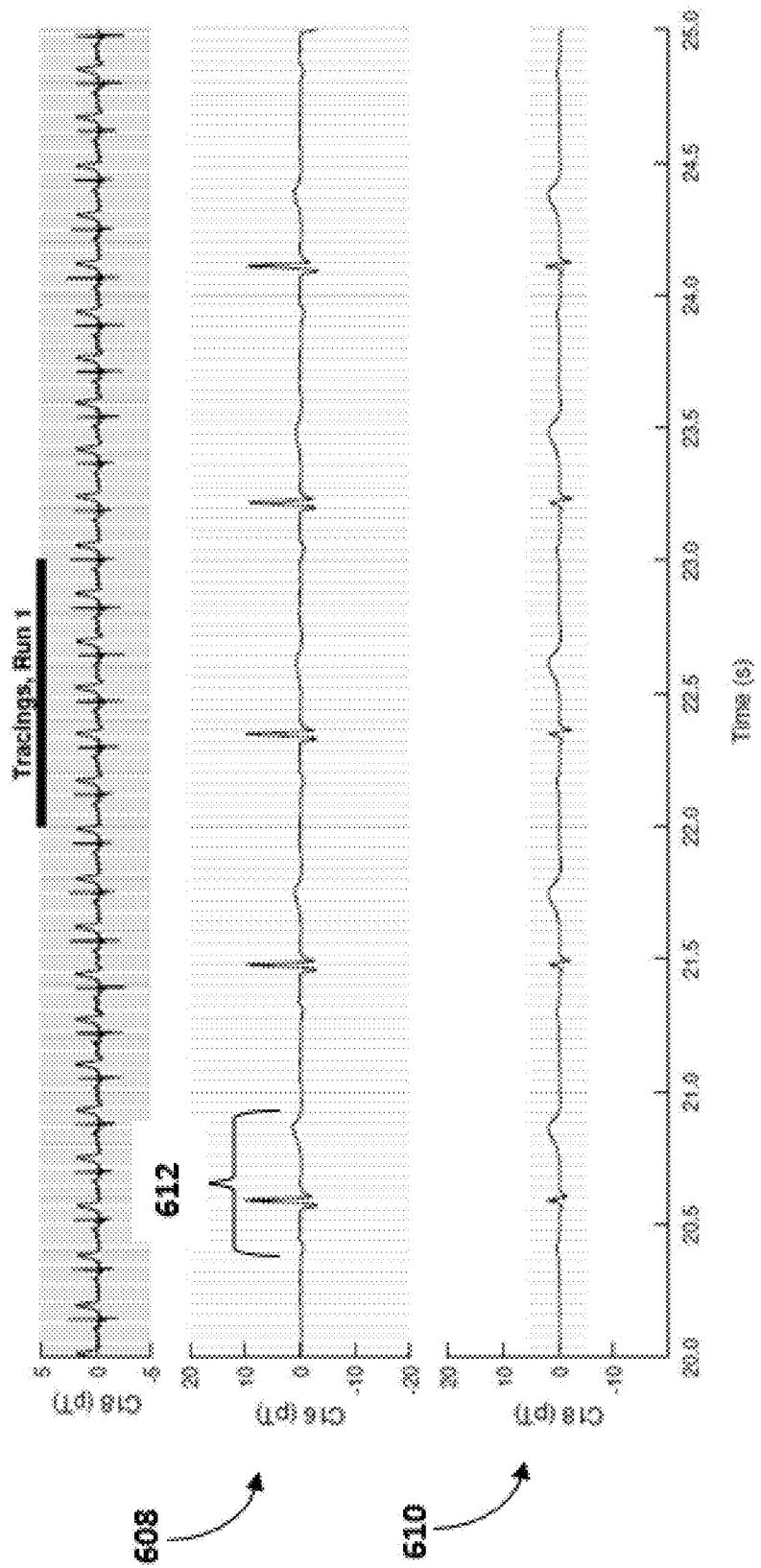

FIG. 6B shows examples of a plurality of single EMF waveforms (as compared to the single waveform of FIG. 6A which comprises a plurality of individual waveforms). In the examples of FIG. 6B, waveforms or tracings 608 and 610 each represent respective EMF signals sensed over the same period of time. In these examples, EMF data is sensed from the same 58 year old male using a plurality of SQUID sensors as in the example of FIG. 6A. In the examples of FIG. 6B, tracings 608 and 610 are each a tracing representing a single waveform sensed over the same period of time and are different at least in part in that each of tracings 608 and 610 correspond to an EMF signal respectively sensed from a different SQUID located at a different position relative to the chest (and therefore the heart) of the individual. That is, tracing 608 corresponds to a first EMF signal sensed from a first SQUID sensor and tracing 610 corresponds to a second EMF signal sensed from a second SQUID sensor where each of the first and second SQUID sensors are located at different positions relative to the heart of the individual.

In a traditional ECG tracing, ten electrodes positioned at different locations on a body of an individual produce 12 ECG tracings, each corresponding to a different "view" of the heart. A particular ECG lead corresponds to a particular "view" of the heart in that each ECG tracing corresponds to a different spatial relationship between one or more ECG electrodes and the heart of the individual.

Similar to a traditional ECG tracing, each of tracings 608 and 610 represent a different "view" of the heart based on the position of the one or more EMF sensors relative to the chest of the individual. That is, current traveling through the heart of an individual generates a different EMF at different locations and as such is results in different appearing tracings based on the location of a sensor sensing that EMF. The tracings 608 and 610 each comprise a PQRST complex 612 (or, as shown, a plurality of PQRST complexes).

The exemplary data from FIGS. 6A and 6B are provided as input to a machine learning software module described herein. The machine learning software module receives the input and interrelates the data in numerous ways so that input data relating to the individual (including data related to the individual received concurrently to the input as well as data related to the individual received before and subsequent to receiving the input) is associated with the sensed EMF data shown in the examples of FIGS. 6A and 6B.

A machine learning software module as described herein correlates the age (58 years old in these examples) and gender (male in these examples) of the individual with one or more of the tracings 600, 608 and 610. Additional data relating to the individual may be provided that the machine learning software module may decide to correlate with the input as well. Non-limiting examples of the additional data comprises health records for the individual, including diagnoses, medications, lab results other EMF sensed data from the individual.

A machine learning software module as described herein further determines how to interrelate data from this individual and how to interrelate data of other individuals so as to generate a hypothesis function which is used to identify the presence of an abnormality in the individual and/or predict the occurrence of an abnormality in the individual.

Figure 7A:
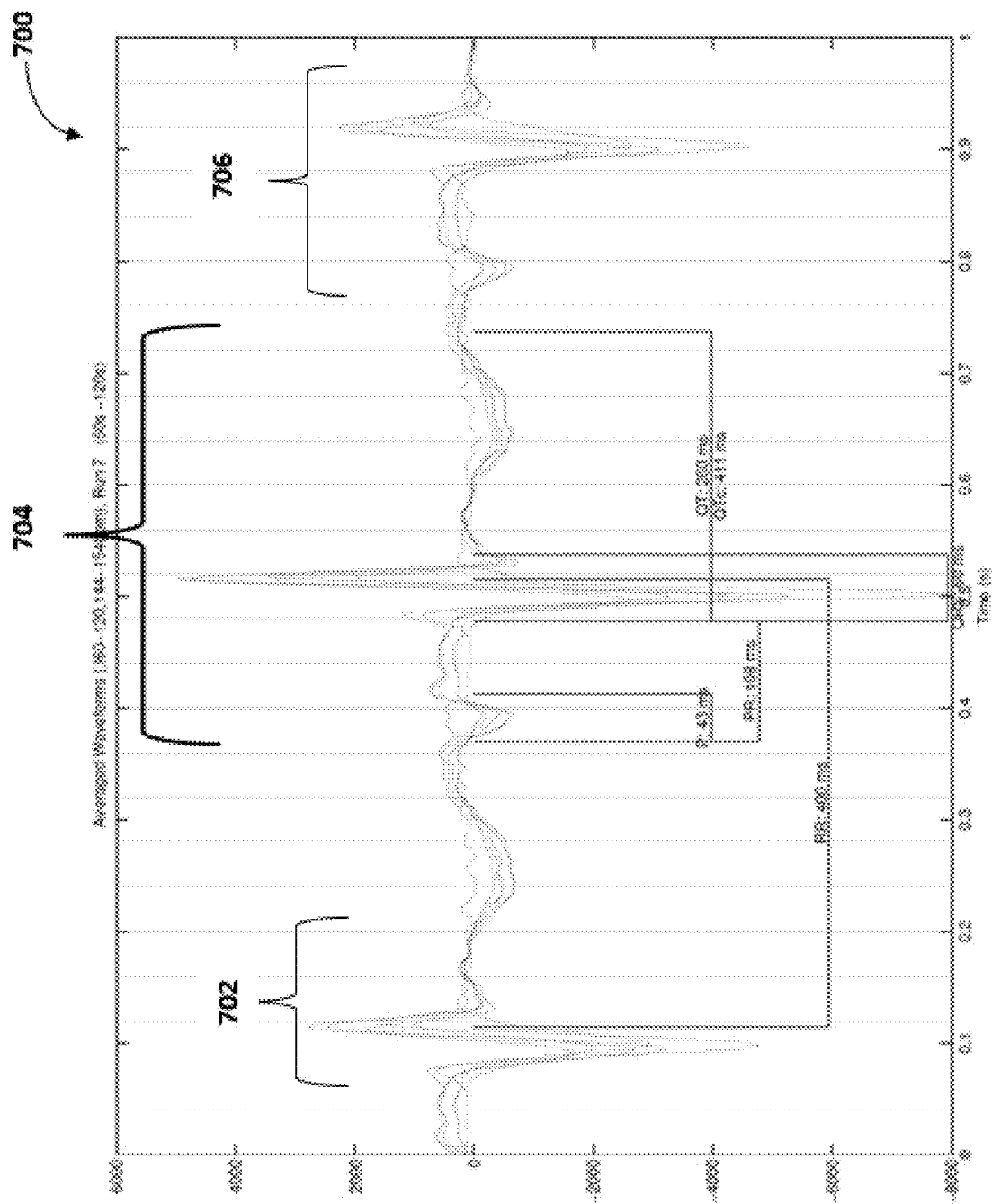
FIGS. 7A and 7B show examples of EMF data sensed from a plurality of OPM sensors positioned within proximity to a fetus.

FIG. 7A shows an example of EMF data sensed from a plurality of OPM sensors positioned within proximity to a heart of a fetus. In this specific example, the EMF data that is sensed is sensed from a 39 weeks and 6 days old fetus using a plurality of OPM sensors positioned in proximity to the fetus. The waveform 700 comprises EMF data in EM units (shown on the Y-axis), said data being sensed over time in seconds (shown on the X-axis).

More specifically, waveform 700 comprises a plurality of waveforms sensed from a plurality of OPM sensors positioned in proximity to the chest of the individual. In the example of FIG. 7A, the plurality of waveforms are positioned at different locations relative to the chest of the individual. In this example, the one or more OPM sensors are positioned in a sensor array where the array is itself positioned in proximity to the chest of the individual so that each of the plurality of OPM sensors is in a different position relative to the chest of the individual (although it should be understood that one or more OPM sensors may be arranged in other configurations in other embodiments of the systems, methods, devices, and software described herein and need not always be arranged in an array). In this example, waveform 700 comprises three separate individual waveforms 702, 704, and, 706. Waveforms 702, 704, and, 706 each correspond to a single PQRST complex as would be seen on a standard ECG. Therefore, each of the waveforms 702, 704, and, 706 correspond to an individual polarization and depolarization cardiac cycle or one heartbeat.

Figure 7B:
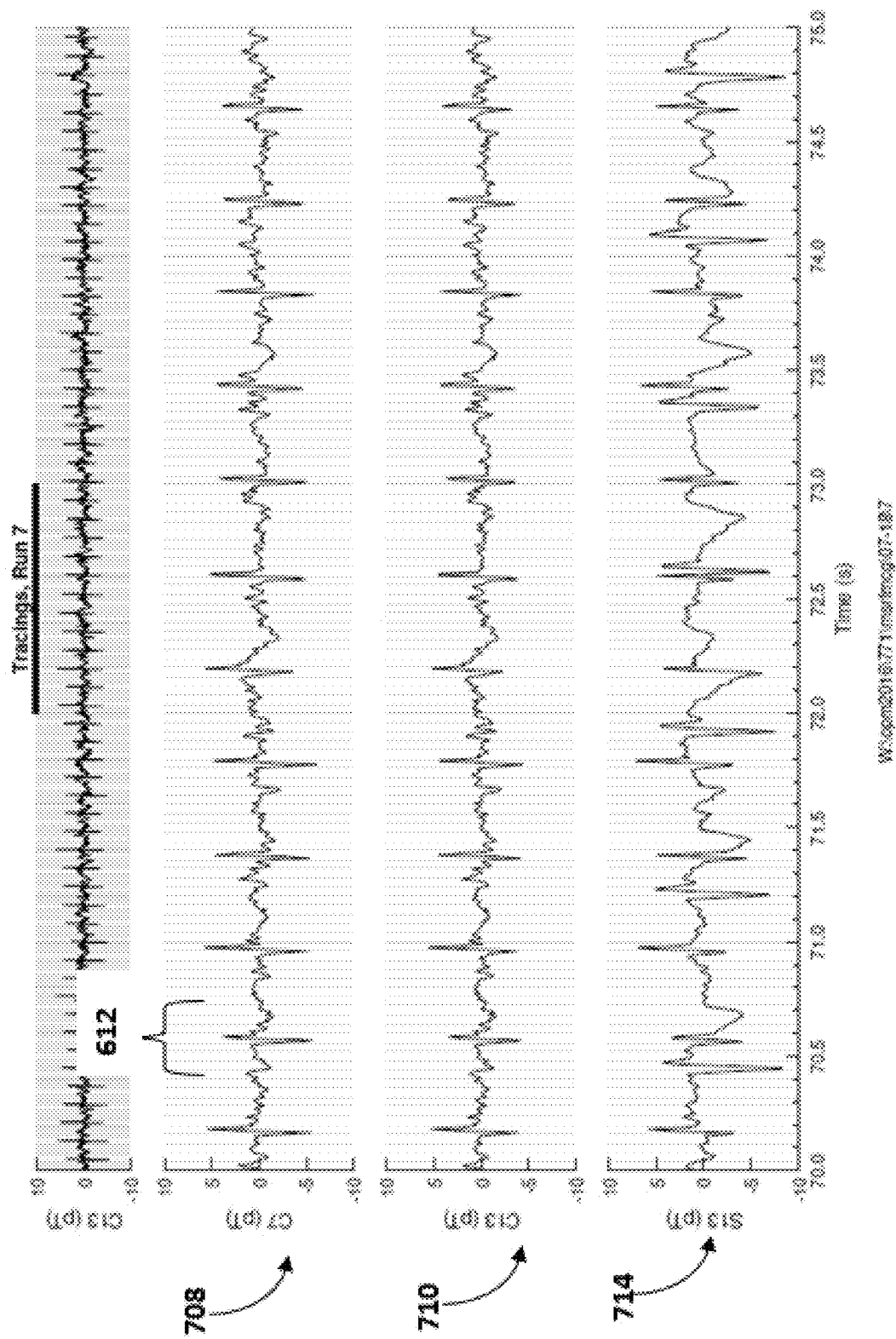

FIG. 7B shows examples of a plurality of single EMF waveforms (as compared to the single waveform of FIG. 7A which comprises a plurality of individual waveforms). In the examples of FIG. 7B, waveforms or tracings 708, 710, and 714 each represent respective EMF signals sensed over the same period of time. In these examples, EMF data is sensed from the same 39 weeks and 6 days old fetus using a plurality of OPM sensors as in the example of FIG. 7A. In the examples of FIG. 7B, tracings 708, 710, and 714 are each a tracing representing a single waveform sensed over the same period of time and are different at least in part in that each of tracings 708, 710, and 714 correspond to an EMF signal respectively sensed from a different OPM located at a different position relative to the chest (and therefore the heart) of the fetus. That is, tracing 708 corresponds to a first EMF signal sensed from a first OPM sensor and tracing 710 corresponds to a second EMF signal sensed from a second OPM sensor where each of the first and second OPM sensors are located at different positions relative to the heart of the fetus.

In a traditional ECG tracing, ten electrodes positioned at different locations on a body of an fetus produce 12 ECG tracings, each corresponding to a different "view" of the heart. A particular ECG lead corresponds to a particular "view" of the heart in that each ECG tracing corresponds to a different spatial relationship between one or more ECG electrodes and the heart of the fetus.

Similar to a traditional ECG tracing, each of tracings 708, 710, and 714 represent a different "view" of the heart based on the position of the one or more EMF sensors relative to the chest of the fetus. That is, current traveling through the heart of an fetus generates a different EMF at different locations and as such is results in different appearing tracings based on the location of a sensor sensing that EMF. The tracings 708, 710, and 714 each comprise a PQRST complex 712 (or, as shown, a plurality of PQRST complexes).

The exemplary data from FIGS. 7A and 7B are provided as input to a machine learning software module described herein. The machine learning software module receives the input and interrelates the data in numerous ways so that input data relating to the fetus (including data related to the fetus received concurrently to the input as well as data related to the fetus received before and subsequent to receiving the input) is associated with the sensed EMF data shown in the examples of FIGS. 7A and 7B.

A machine learning software module as described herein correlates the of the fetus with one or more of the tracings 700, 708, 710, and 714. Additional data relating to the fetus may be provided that the machine learning software module may decide to correlate with the input as well. Non-limiting examples of the additional data comprises health records for the fetus, including diagnoses, medications, lab results other EMF sensed data from the fetus.

A machine learning software module as described herein further determines how to interrelate data from this individual and how to interrelate data of other fetuses so as to generate a hypothesis function which is used to identify the presence of an abnormality in the individual and/or predict the occurrence of an abnormality in the fetus.

Figure 8A:
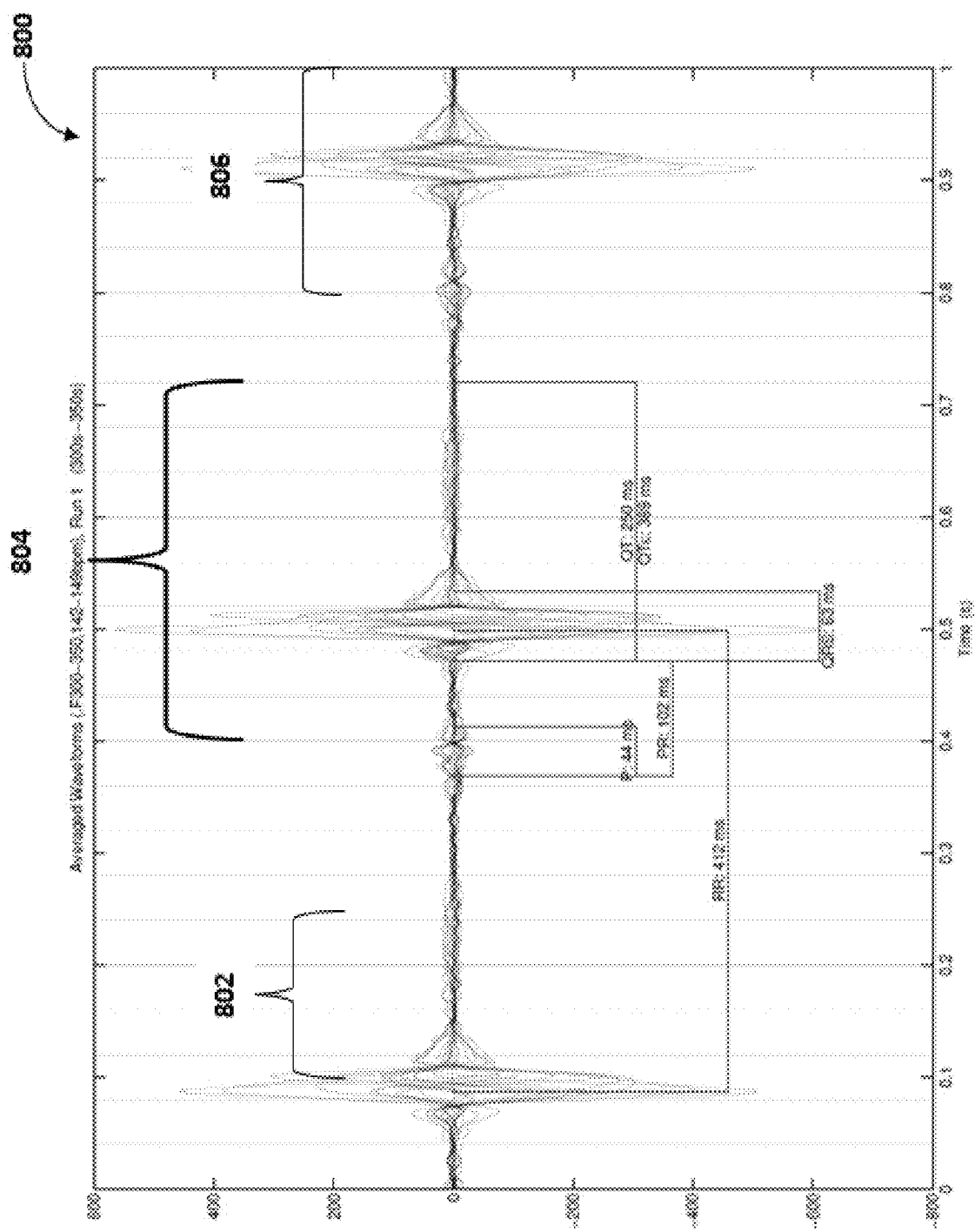
FIGS. 8A and 8B show examples of EMF data sensed from a plurality of SQUID sensors positioned within proximity to a fetus.

FIG. 8A shows an example of EMF data sensed from a plurality of SQUID sensors positioned within proximity to a heart of a fetus. In this specific example, the EMF that data is sensed is from a 39 weeks and 6 days old fetus using a plurality of SQUID sensors positioned in proximity to the fetus. The waveform 800 comprises EMF data in EM units (shown on the Y-axis), said data being sensed over time in seconds (shown on the X-axis).

More specifically, waveform 800 comprises a plurality of waveforms sensed from a plurality of SQUID sensors positioned in proximity to the chest of the individual. In the example of FIG. 8A, the plurality of waveforms are positioned at different locations relative to the chest of the individual. In this example, the one or more SQUID sensors are positioned in a sensor array where the array is itself positioned in proximity to the chest of the individual so that each of the plurality of SQUID sensors is in a different position relative to the chest of the individual (although it should be understood that one or more SQUID sensors may be arranged in other configurations in other embodiments of the systems, methods, devices, and software described herein and need not always be arranged in an array). In this example, waveform 800 comprises three separate individual waveforms 802, 804, and, 806. Waveforms 802, 804, and, 806 each correspond to a single PQRST complex as would be seen on a standard ECG. Therefore, each of the waveforms 802, 804, and, 806 correspond to an individual polarization and depolarization cardiac cycle or one heartbeat.

Figure 8B:
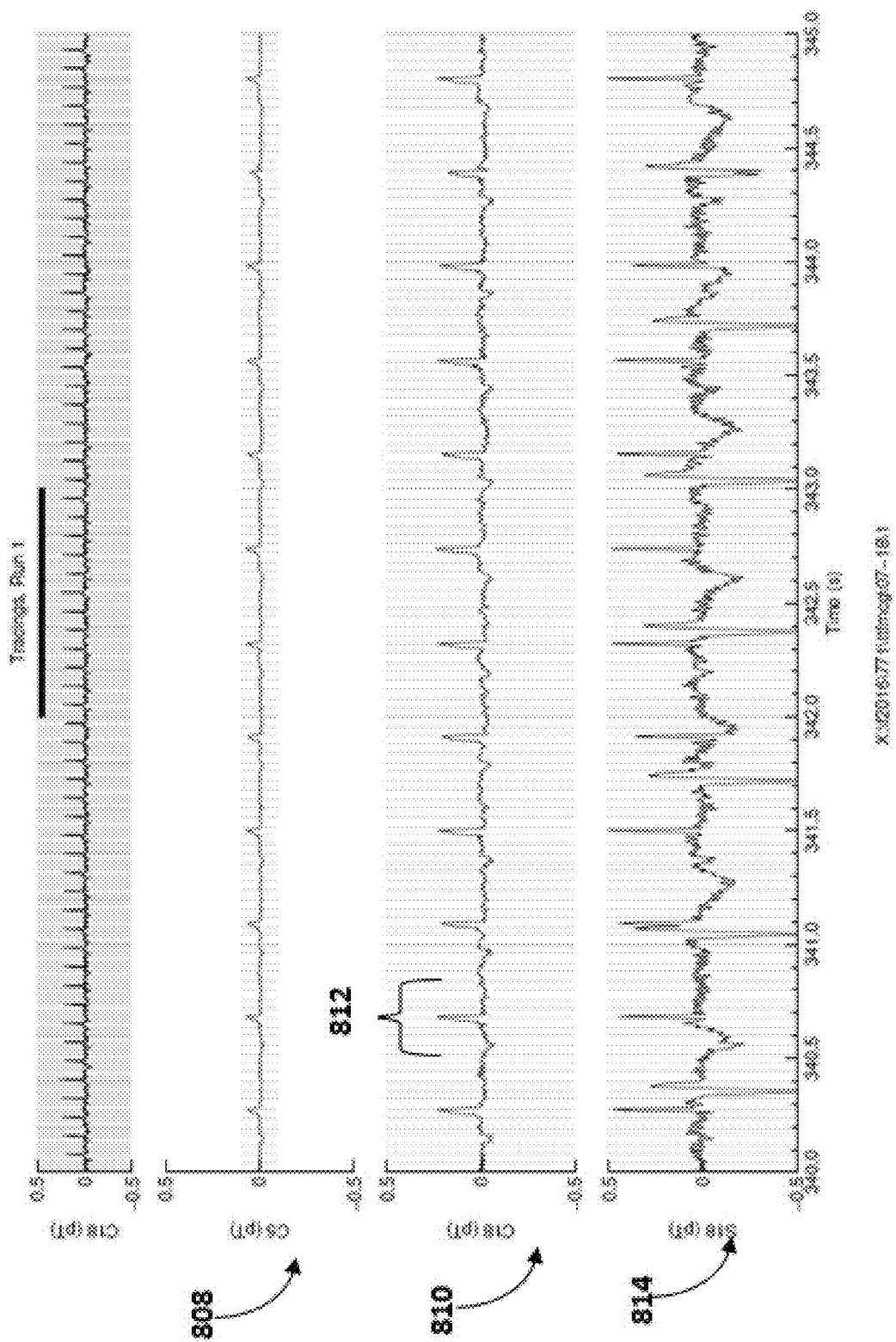

FIG. 8B shows examples of a plurality of single EMF waveforms (as compared to the single waveform of FIG. 8A which comprises a plurality of individual waveforms). In the examples of FIG. 8B, waveforms or tracings 808, 810, and 814 each represent respective EMF signals sensed over the same period of time. In these examples, EMF data is sensed from the same 39 weeks and 6 days old fetus using a plurality of SQUID sensors as in the example of FIG. 8A. In the examples of FIG. 8B, tracings 808, 810, and 814 are each a tracing representing a single waveform sensed over the same period of time and are different at least in part in that each of tracings 808, 810, and 814 correspond to an EMF signal respectively sensed from a different SQUID located at a different position relative to the chest (and therefore the heart) of the fetus. That is, tracing 808 corresponds to a first EMF signal sensed from a first SQUID sensor and tracing 810 corresponds to a second EMF signal sensed from a second SQUID sensor where each of the first and second SQUID sensors are located at different positions relative to the heart of the fetus.

In a traditional ECG tracing, ten electrodes positioned at different locations on a body of an fetus produce 12 ECG tracings, each corresponding to a different "view" of the heart. A particular ECG lead corresponds to a particular "view" of the heart in that each ECG tracing corresponds to a different spatial relationship between one or more ECG electrodes and the heart of the fetus.

Similar to a traditional ECG tracing, each of tracings 808, 810, and 814 represent a different "view" of the heart based on the position of the one or more EMF sensors relative to the chest of the fetus. That is, current traveling through the heart of an fetus generates a different EMF at different locations and as such is results in different appearing tracings based on the location of a sensor sensing that EMF. The tracings 808, 810, and 814 each comprise a PQRST complex 812 (or, as shown, a plurality of PQRST complexes).

The exemplary data from FIGS. 8A and 8B are provided as input to a machine learning software module described herein. The machine learning software module receives the input and interrelates the data in numerous ways so that input data relating to the fetus (including data related to the fetus received concurrently to the input as well as data related to the fetus received before and subsequent to receiving the input) is associated with the sensed EMF data shown in the examples of FIGS. 8A and 8B. A machine learning software module as described herein correlates, for example, the age the fetus with one or more of the tracings 800, 808, 810, and 814. Additional data relating to the fetus may be provided that the machine learning software module may decide to correlate with the input as well. Non-limiting examples of the additional data comprises health records for the fetus, including diagnoses, medications, lab results other EMF sensed data from the fetus.

A machine learning software module as described herein further determines how to interrelate data from this fetus and how to interrelate data of other fetuses so as to generate a hypothesis function which is used to identify the presence of an abnormality in the fetus and/or predict the occurrence of an abnormality in the fetus.

Figure 9:
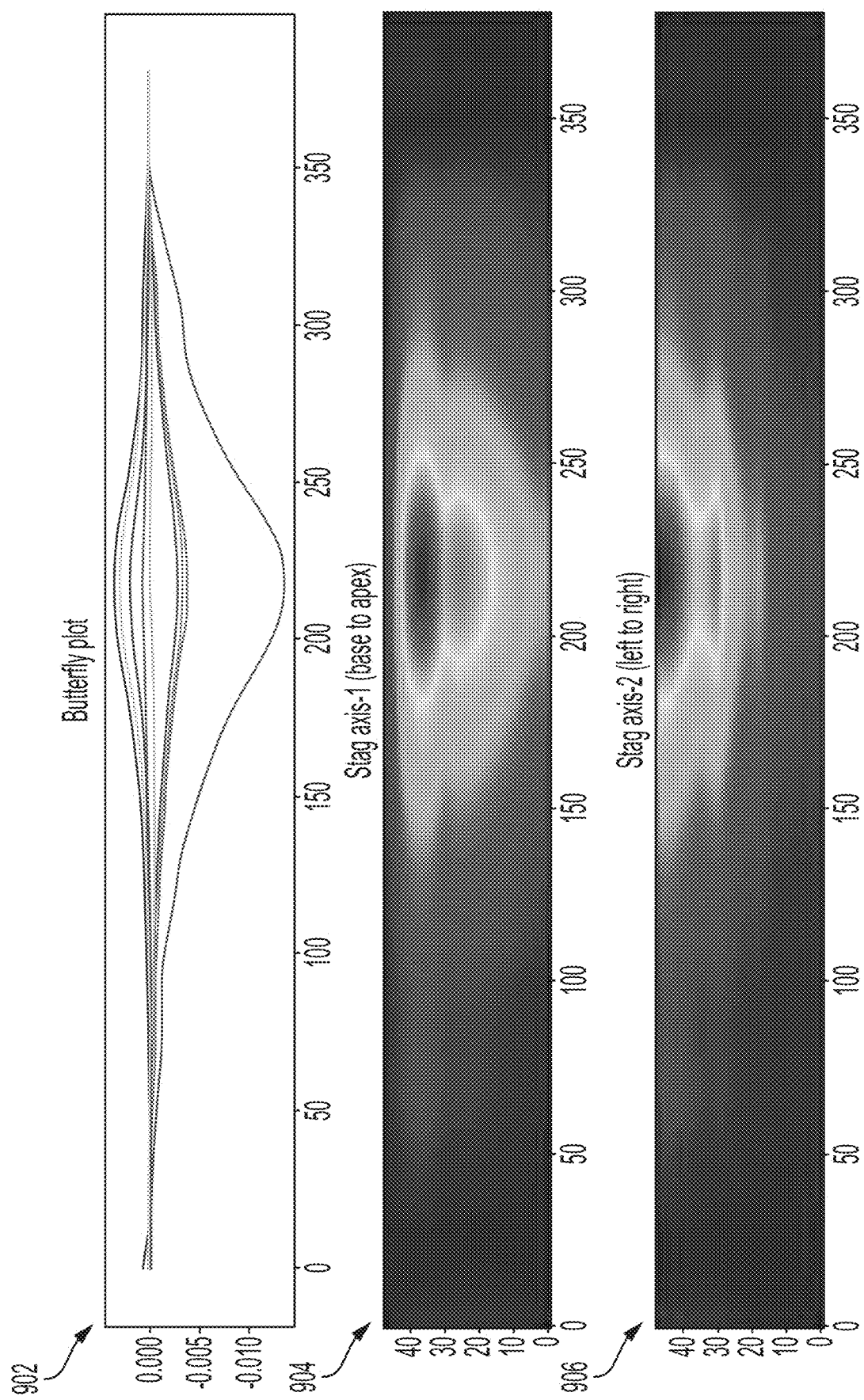
FIG. 9 shows three spatiotemporal activation representations of the magnetic activation of a healthy adult heart.

FIG. 9 shows three spatiotemporal activation representations of the magnetic activation of a healthy adult heart. The first spatiotemporal activation representation 902 comprises a butterfly plot. The second spatiotemporal activation representation 904 comprises a "view" of magnetic activation of a heart from base to apex. The third spatiotemporal activation representation 906 comprises a "view" of magnetic activation of a heart from left to right.

The exemplary data from FIG. 9 is provided as input to a machine learning software module described herein. The machine learning software module receives the input and interrelates the data in numerous ways so that input data relating to the individual from which the data was obtained (including data related to the individual received concurrently to the input as well as data related to the individual received before and subsequent to receiving the input) is associated with other sensed EMF data. A machine learning software module as described herein correlates, for example, the age the individual with other data relating to the individual. Additional data relating to the individual may be provided that the machine learning software module may decide to correlate with the input as well. Non-limiting examples of the additional data comprises health records for the individual, including diagnoses, medications, lab results other EMF sensed data from the individual.

A machine learning software module as described herein further determines how to interrelate data from this individual and how to interrelate data of other individuals so as to generate a hypothesis function which is used to identify the presence of an abnormality in the individual and/or predict the occurrence of an abnormality in the individual.

Brain Analysis

Figure 10:
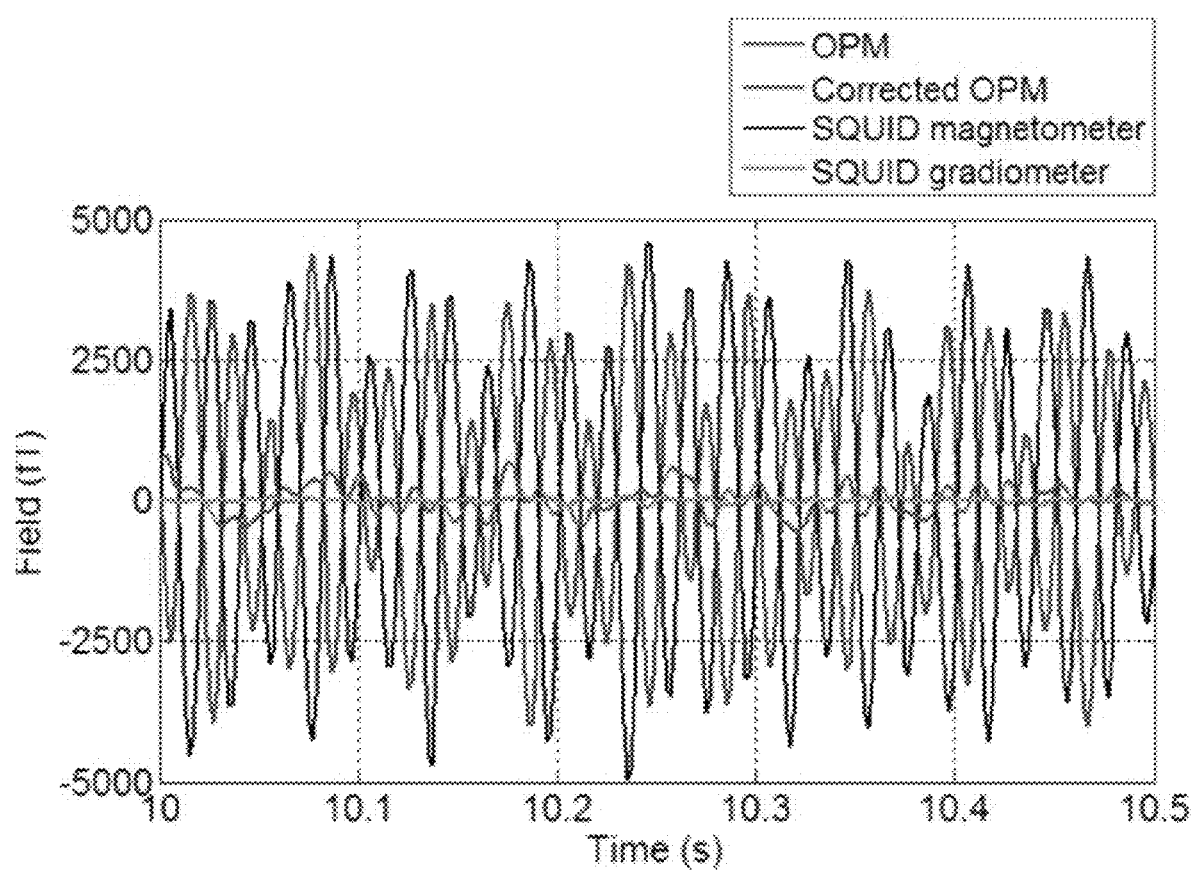
FIG. 10 shows an example of a MEG as sensed from an individual based on a sensed EMF that is sensed in proximity to a head of the individual.

FIG. 10 shows an example of a MEG as sensed from an individual based on a sensed EMF that is sensed in proximity to a head of the individual. In this example, one or more EMF sensors are positioned around a head of an individual. The one or more EMF sensors sense an EMF associated with one or more electric currents generated by the tissue of the brain of the individual. The sensed EMF associated with the electric currents generated by the tissue of the brain of the individual are then converted into one or more waveforms that represent an MEG of the brain of the individual. FIG. 10 shows four different waveforms with EMF values on the Y-axis and time values on the X-axis. A first waveform comprises an EMF associated with the brain of an individual sensed by an OPM sensor. A second waveform comprises an EMF associated with the brain of an individual sensed by an OPM sensor that is further filtered to remove background noise. A third waveform comprises an EMF associated with the brain of an individual sensed by a SQUID magnetometer sensor. A fourth waveform comprises an EMF associated with the brain of an individual sensed by a SQUID gradiometer sensor.

The exemplary data from FIG. 10 is provided as input to a machine learning software module described herein. The machine learning software module receives the input and interrelates the data in numerous ways so that input data relating to the individual from which the data was obtained (including data related to the individual received concurrently to the input as well as data related to the individual received before and subsequent to receiving the input) is associated with other sensed EMF data. A machine learning software module as described herein correlates, for example, the age the individual with other data relating to the individual. Additional data relating to the individual may be provided that the machine learning software module may decide to correlate with the input as well. Non-limiting examples of the additional data comprises health records for the individual, including diagnoses, medications, lab results other EMF sensed data from the individual.

A machine learning software module as described herein further determines how to interrelate data from this individual and how to interrelate data of other individuals so as to generate a hypothesis function which is used to identify the presence of an abnormality in the individual and/or predict the occurrence of an abnormality in the individual.

Figure 11:
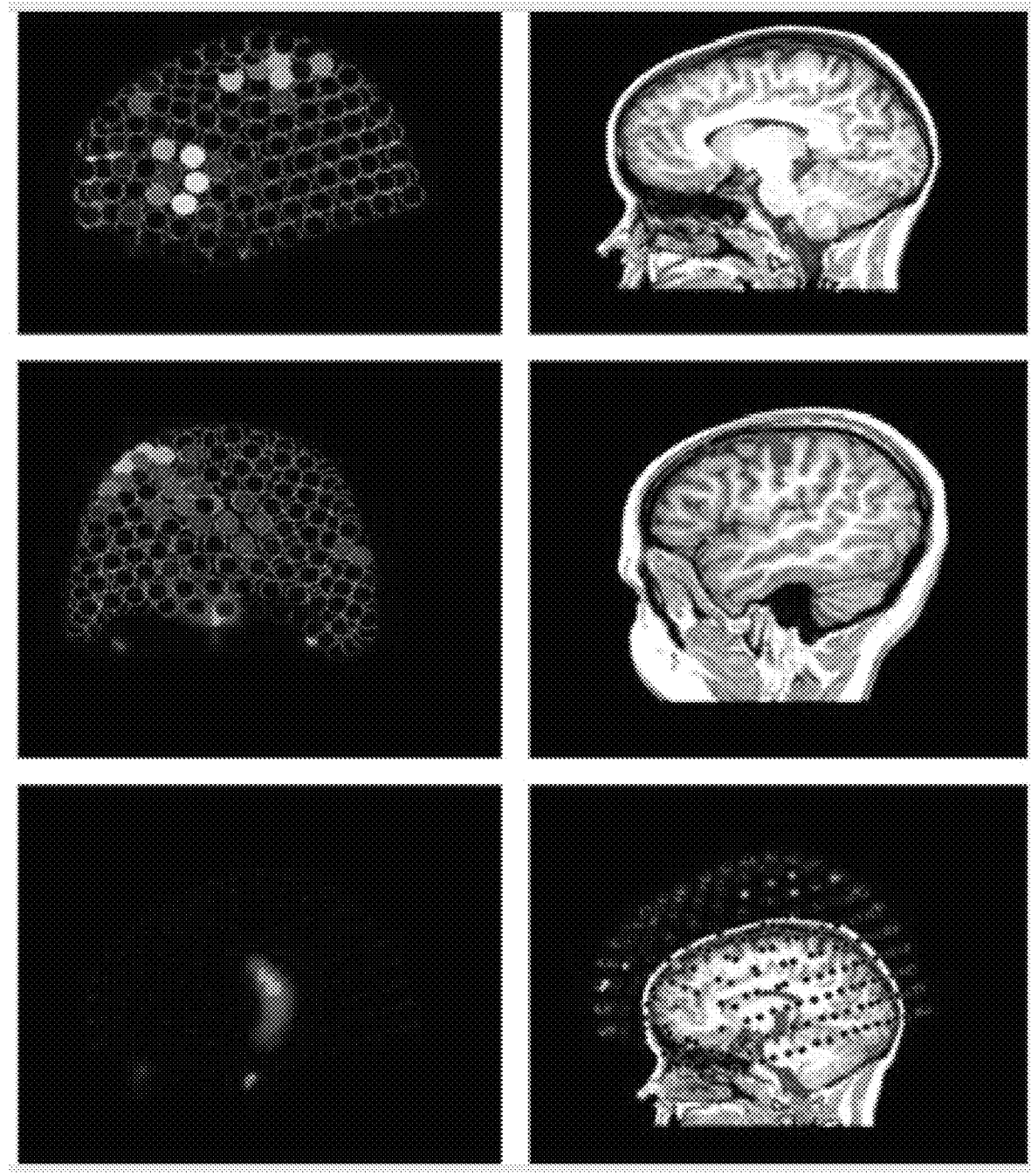
FIG. 11 shows an example of a co-registered Mill and MEG as generated from an EMF sensed from an individual.

FIG. 11 shows an example of a co-registered MRI and MEG as generated from an EMF sensed from an individual. FIG. 11 specifically shows the correlation of brain magnetic field mapping to spatial regions on a medical image of a brain of an individual.

The exemplary data from FIG. 11 is provided as input to a machine learning software module described herein. The machine learning software module receives the input and interrelates the data in numerous ways so that input data relating to the individual from which the data was obtained (including data related to the individual received concurrently to the input as well as data related to the individual received before and subsequent to receiving the input) is associated with other sensed EMF data. A machine learning software module as described herein correlates, for example, the age the individual with other data relating to the individual. Additional data relating to the individual may be provided that the machine learning software module may decide to correlate with the input as well. Non-limiting examples of the additional data comprises health records for the individual, including diagnoses, medications, lab results other EMF sensed data from the individual.

A machine learning software module as described herein further determines how to interrelate data from this individual and how to interrelate data of other individuals so as to generate a hypothesis function which is used to identify the presence of an abnormality in the individual and/or predict the occurrence of an abnormality in the individual.

An Example Demonstrating Training and Prediction

Training Phase:

In an example of a neural network comprising a Deep Neural Network (DNN), the DNN is trained using 10,000 normal EMF data samples which are similar to the data sample of FIG. 9. These data samples are used by the neural network of this example to learn the probability distribution of normal EMF data. At the end of the training phase, the DNN determines or identifies or receives a hypothesis function which allows the DNN to generate high-quality reconstructions of normal repolarization (ST-T) segments from EMF data and minimize the reconstruction error between the original and the reconstructed input of normal EMF data.

Figure 12:
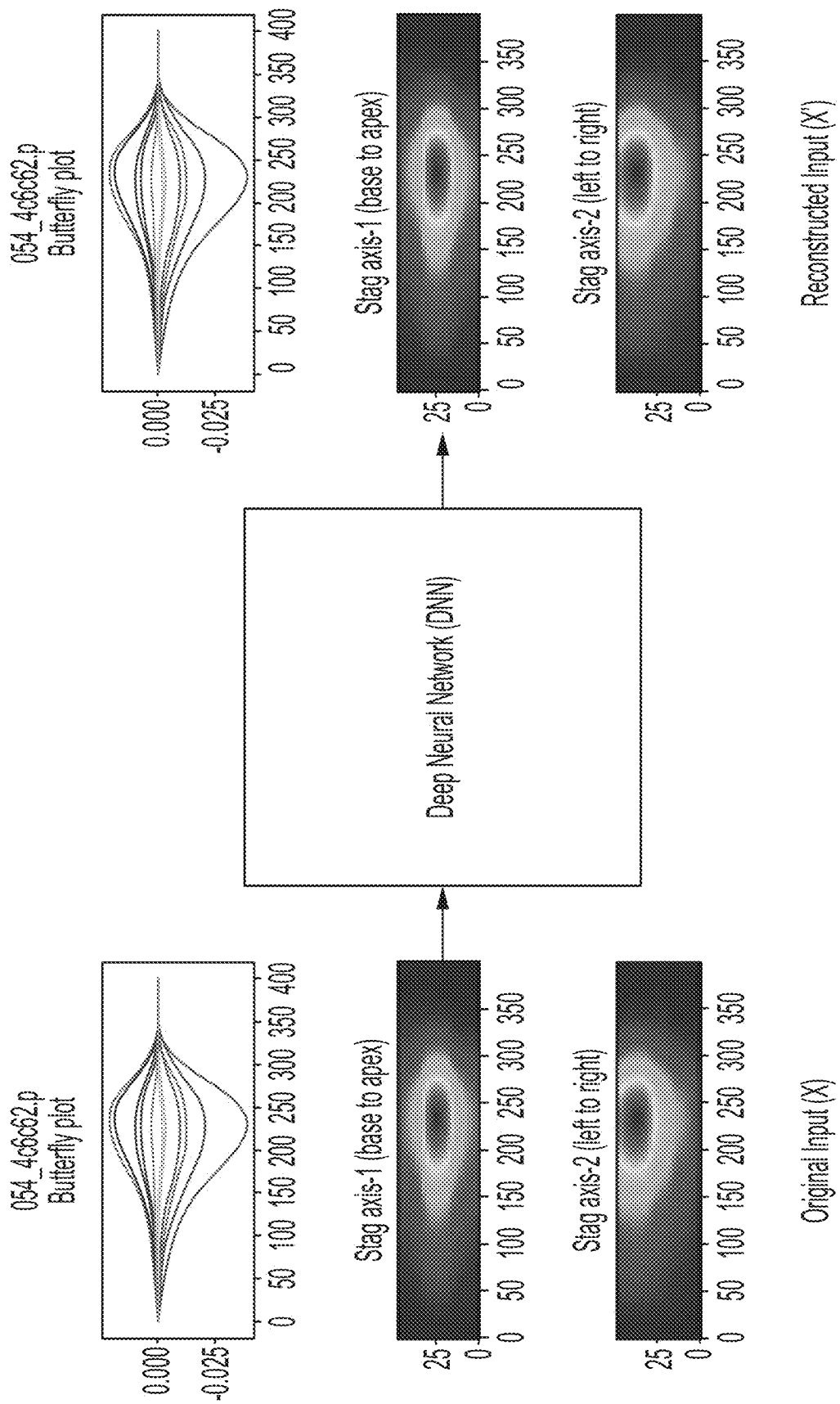
FIG. 12 shows a schematic representation of cardiac related EMF data received by a DNN which is configured to output a reconstruction of that EMF data X'

FIG. 12 shows a schematic representation of cardiac related EMF data received by a DNN which is configured to output a reconstruction of that EMF data $X'$. In this example, a hypothesis function used by the DNN to verify the accuracy of a reconstruction of EMF data compares the sensed input EMF data sample to the reconstruction generated by the DNN and determines a degree of error between the reconstruction and the input EMF data. The degree of error between the reconstruction generated by the DNN and the input EMF data is compared to a threshold value which is generated using the received 10,000 normal EMF data samples.

Prediction Phase:

A prediction phase uses the constructed and optimized hypothesis function from the training phase to predict the probability of an abnormality in an unknown patient's organ or tissue by using the EMF data of the patient.

Based on the learned hypothesis function from the training phase, if the reconstruction error is greater than a particular threshold, the patient EMF data sample is abnormal.

Let T be the threshold, then hypothesis function H is defined as:

$H$=Reconstruction error($E$) between the original input ($X$) and the reconstructed input ($X'$)

$H=E=X-X'$

If $E>=T$---->Abnormal, $E<T$---->Normal

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A diagnostic device configured to detect a cardiac abnormality of a heart of an individual, comprising:
   (i) an electromagnetic field sensor configured to sense an electromagnetic field measurement associated with the heart of the individual;
   (ii) a processor operably coupled to the electromagnetic field sensor; and
   (iii) a non-transitory computer-readable storage medium encoded with software comprising a trained machine learning software module, wherein the trained machine learning software module is configured to process an electromagnetic field measurement of the individual to reconstruct a reference spatiotemporal representation for the individual comprising a spatiotemporal representation of heart-related electromagnetic field (EMF) signal segments that is representative of an absence of the cardiac abnormality, wherein the software is executable by the processor and causes the processor to:
      (a) receive the electromagnetic field measurement from the electromagnetic field sensor;
      (b) generate a test spatiotemporal representation for the individual using the electromagnetic field measurement, wherein the test spatiotemporal representation comprises (i) a spatiotemporal representation of magnetic activation of the heart from base to apex, or (ii) a spatiotemporal representation of magnetic activation of the heart from left to right;
      (c) process the electromagnetic field measurement using the trained machine learning software module to reconstruct the reference spatiotemporal representation for the individual comprising the spatiotemporal representation of heart-related EMF signal segments that is representative of the absence of the cardiac abnormality;
      (d) determining a difference between the test spatiotemporal representation for the individual and the reference spatiotemporal representation for the individual;
      (e) detect the cardiac abnormality of the heart of the individual based at least in part on the difference determined in (d); and
      (f) generate an output based on the detection, the output including one or more of an abnormality, a disease state, an imbalance, a diagnosis, a prognosis, a prediction of a change in health status, or a therapy suggestion including preventative therapy for the individual.

2. The device of claim 1, further comprising a plurality of electromagnetic field sensors configured to be positioned at a plurality of different positions relative to a body of the individual to sense a plurality of electromagnetic field measurements associated with the individual.

3. The device of claim 1, further comprising a housing containing the processor, wherein the electromagnetic field sensor is hard-connected to the housing.

4. The device of claim 1, wherein the trained machine learning software module is trained using a plurality of electromagnetic field values sensed from a plurality of individuals.

5. The device of claim 4, wherein the trained machine learning software module is trained using a plurality of health data values associated with the plurality of individuals.

6. The device of claim 4, wherein the plurality of electromagnetic field values sensed from the plurality of individuals comprises heart-related data.

7. The device of claim 1, wherein the trained machine learning software module is trained using one or more of demographic data, medical image data, and clinical data associated with one or more individuals.

8. The device of claim 1, wherein the software is executable by the processor and causes the processor to further determine a therapy for treating the individual based on the detection of the cardiac abnormality.

9. The device of claim 1, wherein the trained machine learning software module comprises a deep neural network (DNN).

10. The device of claim 9, wherein the DNN comprises a deep convolutional neural network (CNN), a deep dilated CNN, a deep fully-connected neural network, or a deep recurrent neural network (RNN).

11. The device of claim 1, wherein the test spatiotemporal representation further comprises both (i) the spatiotemporal representation of magnetic activation of the heart from base to apex, and (ii) the spatiotemporal representation of magnetic activation of the heart from left to right.

12. The device of claim 11, wherein the test spatiotemporal representation further comprises a butterfly plot.

13. The device of claim 1, wherein an abnormal medical diagnosis for the individual is determined when the difference determined in (d) is greater than or equal to a threshold value, and wherein a normal medical diagnosis for the individual is determined when the difference determined in (d) is less than the threshold value.

14. The device of claim 1, wherein the electromagnetic field sensor comprises an optically pumped magnetometer (OPM), a fluxgate, or a superconducting quantum interference device (SQUID).

15. The device of claim 14, wherein the electromagnetic field sensor comprises the OPM.

16. The device of claim 14, wherein the electromagnetic field sensor comprises the SQUID.

17. The device of claim 1, wherein the software is executable by the processor and causes the processor to further localize an anatomical region of the heart of the individual associated with the cardiac abnormality.

18. The device of claim 1, wherein the cardiac abnormality of the individual comprises cardiac ischemia.

19. The device of claim 1, wherein the cardiac abnormality of the individual comprises congestive heart failure.

20. A computer-implemented method for detecting a cardiac abnormality of a heart of an individual, comprising:
(a) sensing, by an electromagnetic field sensor, an electromagnetic field measurement associated with the heart of the individual;
(b) generating a test spatiotemporal representation for the individual using the electromagnetic field measurement, wherein the test spatiotemporal representation comprises (i) a spatiotemporal representation of magnetic activation of the heart from base to apex, or (ii) a spatiotemporal representation of magnetic activation of the heart from left to right;
(c) processing the electromagnetic field measurement using a trained machine learning algorithm to reconstruct a reference spatiotemporal representation for the individual comprising a spatiotemporal representation of heart-related EMF signal segments that is representative of an absence of the cardiac abnormality;
(d) determining a difference between the test spatiotemporal representation for the individual and the reference spatiotemporal representation for the individual;
(e) detecting the cardiac abnormality of the heart of the individual based at least in part on the difference determined in (d); and
(f) generating an output based on the detection, the output including one or more of an abnormality. a disease state, an imbalance, a diagnosis, a prognosis, a prediction of a change in health status, or a therapy suggestion including preventative therapy for the individual.

21. A non-transitory computer-readable storage medium comprising machine-executable instructions that, when executed by one or more processors, implements a method for detecting a cardiac abnormality of a heart of an individual, the method comprising:
(a) sensing, by an electromagnetic field sensor, an electromagnetic field measurement associated with the heart of the individual;
(b) generating a test spatiotemporal representation for the individual using the electromagnetic field measurement, wherein the test spatiotemporal representation comprises (i) a spatiotemporal representation of magnetic activation of the heart from base to apex, or (ii) a spatiotemporal representation of magnetic activation of the heart from left to right;
(c) processing the electromagnetic field measurement using a trained machine learning algorithm to reconstruct a reference spatiotemporal representation for the individual comprising a spatiotemporal representation of heart-related EMF signal segments that is representative of an absence of the cardiac abnormality;
(d) determining a difference between the test spatiotemporal representation for the individual and the reference spatiotemporal representation for the individual;
(g) detecting the cardiac abnormality of the heart of the individual based at least in part on the difference determined in (d); and
(h) generating an output based on the detection, the output including one or more of an abnormality, a disease state, an imbalance, a diagnosis, a prognosis, a prediction of a change in health status, or a therapy suggestion including preventative therapy for the individual.

* * * * *